(12) United States Patent
Vaillancourt et al.

(10) Patent No.: US 6,458,788 B1
(45) Date of Patent: Oct. 1, 2002

(54) 4-HYDROXYCINNOLINE-3-CARBOXYAMIDES AS ANTIVIRAL AGENTS

(75) Inventors: Valerie A. Vaillancourt; Scott D. Larsen; Sajiv K. Nair, all of Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 6 days.

(21) Appl. No.: 09/808,902

(22) Filed: Mar. 15, 2001

Related U.S. Application Data

(60) Provisional application No. 60/190,976, filed on Mar. 21, 2000.

(51) Int. Cl.[7] ................ A61K 31/5377; A61P 31/22; C07D 413/02
(52) U.S. Cl. ............... 514/234.5; 544/58.2; 544/113; 544/116; 544/235
(58) Field of Search ................ 544/116, 235; 514/234.5

(56) References Cited

U.S. PATENT DOCUMENTS

| | | | |
|---|---|---|---|
| 4,559,157 A | 12/1985 | Smith et al. | |
| 4,568,649 A | 2/1986 | Bertoglio-Matte | |
| 4,608,392 A | 8/1986 | Jacquet et al. | |
| 4,820,508 A | 4/1989 | Wortzman | |
| 4,826,837 A | * 5/1989 | Doria et al. | 514/248 |
| 4,886,800 A | 12/1989 | Resch | |
| 4,938,949 A | 7/1990 | Borch et al. | |
| 4,992,478 A | 2/1991 | Geria | |
| 5,753,666 A | 5/1998 | Beasley et al. | |
| 5,891,878 A | 4/1999 | Beasley et al. | |
| 6,093,732 A | * 7/2000 | Tucker et al. | 514/312 |

FOREIGN PATENT DOCUMENTS

| | | |
|---|---|---|
| EP | 0277791 | 8/1988 |
| WO | WO97/04775 | 2/1997 |
| WO | WO99/32450 | 7/1999 |
| WO | WO99/38867 | 8/1999 |

OTHER PUBLICATIONS

Barber, HJ. *Journal of the Chemical Society*, A New Cinnoline Synthesis. Part I. Cyclisation of Mesoxalyl Chloride Phenylhydrazones to give Substituted 4–Hydroxycinnoline–3–carboxylic Acids. pp. 2828–2843, 1961.

Cook, N.D., et al., *Pharmaceutical Manufacturing International*. pp. 49–53, 1992.

Miyamoto, Teruyuki, *Chem Parm Bull*, A new Cinnoline Ring Construction by the Reaction of 2–Diazo–3–(2–fluorophenyl)–3–oxopropionates with Tri–n–butylphosphine. vol. 38 No. 4 pp. 1321–1327, 1988.

*Organic Preparations and Procedures International*. vol. 13, pp. 112, 1981.

Takeuchi, K. *Laboratory Practice*, Sep. issue, 1992.

\* cited by examiner

*Primary Examiner*—Robert W. Ramsuer
(74) *Attorney, Agent, or Firm*—Lucy X. Yang; Andrew M. Solomon

(57) ABSTRACT

Certain novel 4-hydroxycinnoline-3-carboxyamides. The compounds are particularly effective in the treatment or prevention of viral infections, particularly infections caused by herpes viruses including herpes simplex virus types 1 and 2, human herpes virus types 6, 7 and 8, varicello zoster virus, human cytomegalovirus or Epstein-Barr virus.

20 Claims, No Drawings

4-HYDROXYCINNOLINE-3-CARBOXYAMIDES AS ANTIVIRAL AGENTS

CROSS-REFERENCE TO RELATED APPLICATIONS

This application claims the benefit of the following provisional application: U.S. Ser. No. 60/190,976, filed Mar. 21, 2000.

BACKGROUND OF THE INVENTION

1. Field of the Invention

The present invention provides novel cinnolines, which are useful as antiviral agents (e.g. as agents against viruses of the herpes family).

2. Technology Description

The herpesviruses comprise a large family of double stranded DNA viruses. They are also a source of the most common viral illnesses in man. Eight of the herpes viruses, herpes simplex virus types 1 and 2 (HSV-1 and HSV-2), varicella zoster virus (VZV), human cytomegalovirus (HCMV), epstein-Barr virus (EBV), and human herpes viruses 6, 7, and 8 (HHV-6, HHV-7, and HHV-8), have been shown to infect humans.

HSV-1 and HSV-2 cause herpetic lesions on the lips and genitals, respectively. They also occasionally cause infections of the eye and encephalitis. HCMV causes birth defects in infants and a variety of diseases in immunocompromised patients such as retinitis, pneumonia, and gastrointestinal disease. VZV is the causative agent of chicken pox and shingles. EBV causes infections mononucleosis. It can also cause lymphomas in immunocompromised patients and has been associated with Burkitt's lymphoma, nasopharyngeal carcinoma, and Hodgkins disease. HHV-6 is the causative agent of roseola and may be associated with multiple sclerosis and chronic fatigue syndrome. HHV-7 disease association is unclear, but it may be involved in some cases of roseola. HHV-8 has been associated with Karposi's sarcoma, body cavity based lymphomas, and multiple myeloma.

U.S. Pat. No. 4,826,837 discloses 4-hydroxycinnoline-3-carboxamides and their use for the treatment of neoplastic diseases and acute and chronic infections of both bacterial and viral origin in mammals.

U.S. Pat. No. 4,886,800 discloses 4-substituted-cinnoline-3-carboxylic acids and 3-acyl-4-substituted-cinnoline derivatives and their use as central nervous system depressants.

U.S. Pat. Nos. 5,753,666 and 5,891,878 and WO 97/04775 disclose 1-alkyl-substituted-quinolone-3-carboxamides that are alleged to have therapeutic utility via inhibition of Phosphodiesterase IV esterase and/or Tumor Necrosis factor activity.

WO 99/38867 discloses 1-cycloalkyl-1,8-naphthyridin-4-one derivatives; pharmacologically acceptable salts or solvates thereof; and a phosphodiesterase IV inhibitor containing any of the above as an active ingredient.

Commonly assigned PCT/U.S. 98/25192 discloses 4-hydroxyquinoline-3-carboxamides and hydrazides as antiviral agents.

Despite the above teachings, there still exists a need in the art for novel compounds that demonstrate desirable antiviral activity.

BRIEF SUMMARY OF THE INVENTION

In accordance with the present invention, novel compounds which demonstrate antiviral activity are provided.

More specifically, the compounds are 4-hydroxy-3-cinnolinecarboxamides which are useful as antiviral agents, particularly against herpes viruses.

Even more specifically, the compounds are of formula (II)

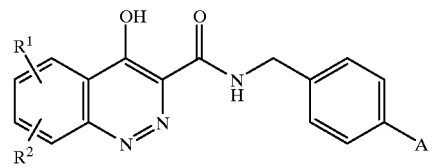

II or a pharmaceutically acceptable salt thereof wherein,

A is
- (a) Cl,
- (b) Br,
- (c) CN,
- (d) $NO_2$, or
- (e) F;

$R^1$ is
- (a) aryl,
- (b) $S(O)_m R^6$,
- (c) (C=O)R, with the proviso that if $R^6$ is $NR^7R^8$, then $R^7$ and $R^8$ do not both equal H
- (d) (C=O)$OR^9$,
- (e) cyano,
- (f) het, wherein said het is bound via a carbon atom,
- (g) Ohet,
- (h) $NR^7R^8$ with the proviso that $R^7$ and $R^8$ do not both equal H
- (i) $SR^{10}$,
- (j) Shet,
- (k) $NHCOR^{12}$,
- (l) $NHSO_2R^{12}$,
- (m) $C_{1-7}$alkyl which is partially unsaturated and optionally substituted by one or more substituents of the group $R^{11}$, $OR^{13}$, $SR^{10}$, $SR^{13}$, $NR^7R^8$, halo, (C=O)$C_{1-7}$alkyl, or $SO_m R^9$, or
- (n) $C_{1-7}$alkyl which is substituted by one or more substituents of the group $R^{11}$, $OR^{13}$, $SR^{10}$, $SR^{13}$, $NR^7R^8$, halo, (C=O)$C_{1-7}$alkyl, or $SO_m R^9$;

$R^2$ is
- (a) H,
- (b) halo,
- (c) aryl,
- (d) $S(O)_m R^6$,
- (e) (C=O)$R^6$,
- (f) (C=O)$OR^9$,
- (g) cyano,
- (h) het, wherein said het is bound via a carbon atom,
- (i) $OR^{10}$,
- (j) Ohet,
- (k) $NR^7R^8$,
- (l) $SR^{10}$,
- (m) Shet,
- (n) $NHCOR^{12}$,
- (o) $NHSO_2R^{12}$, or
- (p) $C_{1-7}$alkyl which may be partially unsaturated and optionally substituted by one or more substituents of the group $R^{11}$, $OR^{13}$, $SR^{10}$, $SR^{13}$, $NR^7R^8$, halo, (C=O)$C_{1-7}$alkyl, or $SO_m R^9$, or
- (q) $R^1$ together with $R^2$ form a carbocyclic or het which may be optionally substituted by $NR^7R^8$, or $C_{1-7}$alkyl which may be optionally substituted by $OR^{14}$;

$R^6$ is
  - (a) $C_{1-7}$alkyl,
  - (b) $NR^7R^8$
  - (c) aryl, or
  - (d) het, wherein said het is bound via a carbon atom;

$R^7$ and $R^8$ are independently
  - (a) H,
  - (b) aryl,
  - (c) $C_{1-7}$alkyl which may be partially unsaturated and is optionally substituted by one or more substituents selected from $NR^{10}R^{10}$, $R^{11}$, $SO_mR^9$, $CONR^{10}OR^{10}O$, or halo, or,
  - (d) $R^7$ and $R^8$ together with the nitrogen to which they are attached form a het;

$R^9$ is
  - (a) aryl,
  - (b) het,
  - (c) $C_{3-8}$cycloalkyl,
  - (d) methyl, or
  - (e) $C_{2-7}$alkyl which may be partially unsaturated and is optionally substituted by one or more substituents selected from $NR^{10}R^{10}$, $R^{11}$, SH, $CONR^{10}R^{10}$, or halo;

$R^{10}$ is
  - (a) H,
  - (b) methyl, or
  - (c) $C_{2-7}$alkyl optionally substituted by OH;

$R^{11}$ is
  - (a) $OR^{10}$,
  - (b) Ohet,
  - (c) Oaryl,
  - (d) $CO_2R^{10}$,
  - (e) het,
  - (f) aryl,
  - (g) CN, or
  - (h) $C_{3-8}$cycloalkyl which may be partially unsaturated and optionally substituted by one or more substituents seleted from a group consisting of $R^{11}$, $NR^7R^8$, $SO_mR^9$, or $C_{1-7}$alkyl optionally substituted by $R^{11}$, $NR^7R8$, or $SO_mR^9$;

$R^{12}$ is
  - (a) H,
  - (b) het,
  - (c) aryl,
  - (d) $C_{3-8}$cycloalkyl,
  - (e) methyl, or
  - (f) $C_{2-7}$alkyl optionally substituted by $NR^7R^8$ or $R^{11}$;

$R^{13}$ is
  - (a) $(P=O)(OR^{14})_2$,
  - (b) $CO(CH_2)_nCON(CH_3)-(CH_2)_nSO_3^-M^+$,
  - (c) an amino acid,
  - (d) C(=O)aryl, or
  - (e) C(=O)$C_{1-7}$alkyl optionally substituted by $NR^7R^8$, aryl, het, $CO_2H$, or $O(CH_2)_nCO_2R^{14}$;

$R^{14}$ is
  - (a) H, or
  - (b) $C_{1-7}$alkyl;

each n is independently 1, 2, 3, 4 or 5;
each m is independently 0, 1, or 2;
M is sodium, potassium, or lithium;
aryl is a phenyl radical or an ortho-fused bicyclic carbocyclic radical wherein at least one ring is aromatic;
wherein any aryl is optionally substituted with one or more substituents selected from the group consisting of halo, OH, cyano, $CO_2R^{14}$, $CF_3$, $C_{1-6}$alkoxy, and $C_{1-6}$ alkyl which may be further substituted by one to three $SR^{14}$, $NR^{14}R^{14}$, $OR^{14}$, or $CO_2R^{14}$ groups;

het is a four- (4), five- (5), six- (6), or seven- (7) membered saturated or unsaturated heterocyclic ring having 1, 2, or 3 heteroatoms selected from the group consisting of oxygen, sulfur, and nitrogen, which is optionally fused to a benzene ring, or any bicyclic heterocycle group;

wherein any het is optionally substituted with one or more substituents selected from the group consisting of halo, OH, cyano, phenyl, $CO_2R^{14}$, $CF_3$, $C_{1-6}$alkoxy, oxo, oxime, and $C_{1-6}$ alkyl which may be further substituted by one to three $SR^{14}$, $NR^{14}R^{14}$, $OR^{14}$, or $CO_2R^{14}$ groups.

In particularly preferred embodiments, $R^1$ is either $CH_2$-morpholine, $CH_2$-(tetrahydro-2H-pyran-4-yl), alkynl-$CH_2OH$ or $(CH_2)_3OH$.

Another embodiment of the present invention provides a pharmaceutical composition comprising a compound of formula (II) as defined above, or a pharmaceutically acceptable salt thereof, and a pharmaceutically acceptable carrier. In preferred embodiments, the composition preferably comprises a therapeutically effective amount of the compound or salt.

Still another embodiment of the present invention provides a method for treating a disease or condition in a mammal caused by a viral infection, particularly a herpes viral infection, comprising administering to the mammal a therapeutically effective amount of a compound of formula (II) or a pharmaceutically acceptable salt thereof.

A further embodiment of the present invention comprises the use of a compound of formula (II) or a pharmaceutically acceptable salt thereof to prepare a medicament for treating or preventing diseases or disorders caused by a viral infection, and particularly a herpes viral infection.

A final embodiment of the present invention comprises a method for inhibiting a viral DNA polymerase, comprising contacting (in vitro or in vivo) the polymerase with an effective inhibitory amount of a compound of formula (11) or a pharmaceutically acceptable salt thereof.

An object of the present invention is to provide novel compounds having biological activity.

A further object of the present invention is to provide novel pharmaceutical compositions.

Still another object of the present invention is to provide a method for treating a disease or condition in a mammal caused by a viral infection, particularly a herpes virus infection.

Another object of the present invention is to provide a method for inhibiting a viral DNA polymerase.

These, and other objects, will readily be apparent to those skilled in the art as reference is made to the detailed description of the preferred embodiment.

DETAILED DESCRIPTION OF THE PREFERRED EMBODIMENT

In describing the preferred embodiment, certain terminology will be utilized for the sake of clarity. Such terminology is intended to encompass the recited embodiment, as well as all technical equivalents which operate in a similar manner for a similar purpose to achieve a similar result.

1. Terminology Definitions

The following definitions are used, unless otherwise described: halo is fluoro, chloro, bromo, or iodo. Alkyl denotes both straight and branched groups; but reference to an individual radical such as "propyl" embraces only the straight chain radical, a branched chain isomer such as "isopropyl" being specifically referred to. When alkyl can be partially unsaturated, the alkyl chain may comprise one or more (e.g. 1, 2, 3, or 4) double or triple bonds in the chain.

Aryl denotes a phenyl radical or an ortho-fused bicyclic carbocyclic radical having about nine to ten ring atoms in which at least one ring is aromatic. Het is a five- (5), six- (6), or seven- (7) membered saturated or unsaturated ring containing 1, 2, 3, or 4 heteroatoms selected from the group consisting of non-peroxide oxygen, sulfur, and nitrogen; as well as a radical of an ortho-fused bicyclic heterocycle of about eight to twelve ring atoms derived therefrom, particularly a benz-derivative or one derived by fusing a propylene, trimethylene, tetramethylene or another monocyclic het diradical thereto. Het includes "heteroaryl," which encompasses a radical attached via a ring carbon of a monocyclic aromatic ring containing five or six ring atoms consisting of carbon and 1, 2, 3, or 4 heteroatoms each selected from the group consisting of non-peroxide oxygen, sulfur, and N(X) wherein X is absent or is H, O, $C_{1-4}$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antiviral activity using the standard tests described herein, or using other similar tests which are well known in the art.

The carbon atom content of various hydrocarbon-containing moieties is indicated by a prefix designating a lower and upper number of carbon atoms in the moiety, i.e., the prefix $C_{i-j}$ indicates a moiety of the integer "i" to the integer "j" carbon atoms, inclusive. Thus, for example, $C_{1-7}$alkyl refers to alkyl of one to seven carbon atoms, inclusive.

To the extent that any pharmaceutically active compound is disclosed or claimed, it is expressly intended to include all active metabolites produced in vivo.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents. The compounds of the invention include compounds of formula (II) having any combination of the values, specific values, more specific values, and preferred values described herein.

2. The Invention

The present invention provides compounds of formula (II):

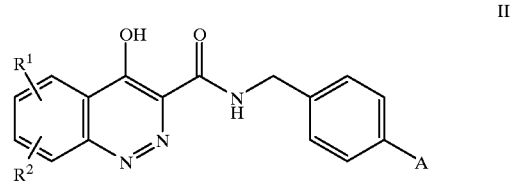

or a pharmaceutically acceptable salt thereof wherein,

A is
(a) Cl,
(b) Br,
(c) CN,
(d) $NO_2$, or
(e) F;

$R^1$ is
(a) aryl,
(b) $S(O)_mR^6$,
(c) $(C=O)R^6$, with the proviso that if $R^6$ is $NR^7R^8$, then $R^7$ and $R^8$ do not both equal H
(d) $(C=O)OR^9$,
(e) cyano,
(f) het, wherein said het is bound via a carbon atom,
(g) Ohet,
(h) $NR^7R^8$ with the proviso that $R^7$ and $R^8$ do not both equal H
(i) $SR^{10}$,
(j) Shet,
(k) $NHCOR^{12}$,
(l) $NHSO_2R^{12}$,
(n) $C_{1-7}$alkyl which is partially unsaturated and optionally substituted by one or more substituents of the group $R^{11}$, $OR^{13}$, $SR^{10}$, $SR^{13}$, $NR^7R^8$, halo, $(C=O)C_{1-7}$alkyl, or $SO_mR^9$, or
(n) $C_{1-7}$alkyl which is substituted by one or more substituents of the group $R^{11}$, $OR^{13}$, $SR^{10}$, $SR^{13}$, $NR^7R^8$, halo, $(C=O)C_{1-7}$alkyl, or $SO_mR^9$;

$R^2$ is
(a) H,
(b) halo,
(c) aryl,
(d) $S(O)_mR^6$,
(e) $(C=O)R^6$,
(f) $(C=O)OR^9$,
(g) cyano,
(h) het, wherein said het is bound via a carbon atom,
(i) $OR^{10}$,
(j) Ohet,
(k) $NR^7R^8$,
(l) $SR^{10}$,
(m) Shet,
(n) $NHCOR^{12}$,
(o) $NHSO_2R^{12}$
(p) $C_{1-7}$alkyl which may be partially unsaturated and optionally substituted by one or more substituents of the group $R^{11}$, $OR^{13}$, $SR^{10}$, $SR^{13}$, $NR^7R^8$, halo, $(C=O)C_{1-7}$alkyl, or $SO_mR^9$, or
(q) $R^1$ together with $R^2$ form a carbocyclic or het which may be optionally substituted by $NR^7R^8$, or $C_{1-7}$alkyl which may be optionally substituted by $OR^{14}$;

$R^6$ is
(a) $C_{1-7}$alkyl,
(b) $NR^7R^8$
(c) aryl, or (d) het, wherein said het is bound via a carbon atom;
$R^7$ and $R^8$ are independently
(a) H,
(b) aryl,
(c) $C_{1-7}$alkyl which may be partially unsaturated and is optionally substituted by one or more substituents selected from $NR^{10}R^{10}$, $R^{11}$, $SO_mR^9$, $CONR^{10}OR^{10}$, or halo, or,
(d) $R^7$ and $R^8$ together with the nitrogen to which they are attached form a het;
$R^9$ is
(a) aryl,
(b) het,
(c) $C_{3-8}$cycloalkyl,
(d) methyl, or
(e) $C_{2-7}$alkyl which may be partially unsaturated and is optionally substituted by one or more substituents selected from $NR^{10}OR^{10}$, $R^{11}$, SH, $CONR^{10}R^{10}$, or halo;
$R^{10}$ is
(a) H,
(b) methyl, or
(c) $C_{2-7}$alkyl optionally substituted by OH;
$R^{11}$ is
(a) $OR^{10}$,
(b) Ohet,
(c) Oaryl,
(d) $CO_2R^{10}$,
(e) het,
(f) aryl,
(g) CN, or
(h) $C_{3-8}$cycloalkyl which may be partially unsaturated and optionally substituted by one or more substituents seleted from a group consisting of $R^{11}$, $NR^7R^8$, $SO_mR^9$, or $C_{1-7}$alkyl optionally substituted by $R^{11}$, $NR^7R8$, or $SO_mR^9$;
$R^{12}$ is
(a) H,
(b) het,
(c) aryl,
(d) $C_{3-8}$cycloalkyl,
(e) methyl, or
(f) $C_{2-7}$alkyl optionally substituted by $NR^7R^8$ or $R^{11}$;
$R^{13}$ is
(a) $(P=O)(OR^{14})_2$,
(b) $CO(CH_2)_nCON(CH_3)—(CH_2)_nSO_3^-M^+$,
(c) an amino acid,
(d) $C(=O)$aryl, or
(e) $C(=O)C_{1-7}$alkyl optionally substituted by $NR^7R^8$, aryl, het, $CO_2H$, or $O(CH_2)_nCO_2R^{14}$;
$R^{14}$ is
(a) H, or
(b) $C_{1-7}$alkyl;
each n is independently 1, 2, 3, 4 or 5;
each m is independently 0, 1, or 2;
M is sodium, potassium, or lithium;
aryl is a phenyl radical or an ortho-fused bicyclic carbocyclic radical wherein at least one ring is aromatic;
wherein any aryl is optionally substituted with one or more substituents selected from the group consisting of halo, OH, cyano, $CO_2R^{14}$, $CF_3$, $C_{1-6}$alkoxy, and $C_{1-6}$ alkyl which may be further substituted by one to three $SR^{14}$, $NR^{14}R^{14,}$ $OR^{14}$, or $CO_2R^{14}$ groups;
het is a four- (4), five- (5), six- (6), or seven- (7) membered saturated or unsaturated heterocyclic ring having 1, 2, or 3 heteroatoms selected from the group consisting of oxygen, sulfur, and nitrogen, which is optionally fused to a benzene ring, or any bicyclic heterocycle group;
wherein any het is optionally substituted with one or more substituents selected from the group consisting of halo, OH, cyano, phenyl, $CO_2R^{14}$, $CF_3$, $C_{1-6}$alkoxy, oxo, oxime, and $C_{1-6}$ alkyl which may be further substituted by one to three $SR^{14}$, $NR^{14}R^{14}$ $OR^{14}$, or $CO_2R^{14}$ groups.

Specifically, $C_{1-7}$alkyl can be methyl, ethyl, propyl, isopropyl, butyl, iso-butyl, sec-butyl, pentyl, 3-pentyl, hexyl, or heptyl; $C_{3-7}$cycloalkyl can be cyclopropyl, cyclobutyl, cyclopentyl, cyclohexyl, or cycloheptyl.

When $C_{1-7}$alkyl is partially unsaturated, it can specifically be vinyl, allyl, 1-propenyl, 2-propenyl, 1-butenyl, 2-butenyl, 3-butenyl, 1,3-butadienyl, 1-pentenyl, 2-pentenyl, 3-pentenyl, 4-pentenyl, 1-hexenyl, 2-hexenyl, 3-hexenyl, 4-hexenyl, 5-hexenyl, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 4-hexynyl, or 5-hexynyl.

Particularly preferred compounds are those where A is Cl and $R^1$ is either $CH_2$-morpholine, alkynl-$CH_2OH$, $CH_2$-(tetrahydro-2H-pyran-4-yl), or $(CH_2)_3OH$.

Specifically preferred compounds include, but are not limited to the following:

N-(4-chlorobenzyl)-4-hydroxy-6-(tetrahydro-2H-pyran-4-ylmethyl)-3-cinnolinecarboxamide;

N-(4-chlorobenzyl)-4-hydroxy-6-(4-morpholinylmethyl)-3-cinnolinecarboxamide;

Methyl 3-{[(4-chlorobenzyl)amino]carbonyl}-4-hydroxy-6-cinnolinecarboxylate;

N-(4-chlorobenzyl)-4-hydroxy-6-(hydroxymethyl)-3-cinnolinecarboxamide;

N-(4-chlorobenzyl)-8-(cyclopropylethynyl)-4-hydroxy-6-(4-morpholinylmethyl)-3-cinnolinecarboxamide;

N-(4-chlorobenzyl)-8-[3-(dimethylamino)-1-propynyl]-4-hydroxy-6-(4-morpholinylmethyl)-3-cinnolinecarboxamide;

N-(4-chlorobenzyl)-4-hydroxy-8-(4-hydroxy-1-butynyl)-6-(4-morpholinylmethyl)-3-cinnolinecarboxamide;

N-(4-chlorobenzyl)-4-hydroxy-8-[(1-hydroxycyclohexyl)ethynyl]-6-(4-morpholinylmethyl)-3-cinnolinecarboxamide;

N-(4-chlorobenzyl)-8-(3,3-dicyclopropyl-3-hydroxy-1-propynyl)-4-hydroxy-6-(4-morpholinylmethyl)-3-cinnolinecarboxamide;

N-(4-chlorobenzyl)-4-hydroxy-8-[(3S)-3-hydroxy-1-butynyl]-6-(4-morpholinylmethyl)-3-cinnolinecarboxamide;

8-{3-[(aminocarbonyl)amino]-3-methyl-1-butynyl}-N-(4-chlorobenzyl)-4-hydroxy-6-(4-morpholinylmethyl)-3-cinnolinecarboxamide;

N-(4-chlorobenzyl)-4-hydroxy-8-[3-methyl-3-(4-thioxo-1,3,5-triazinan-1-yl)-1-butynyl]-6-(4-morpholinylmethyl)-3-cinnolinecarboxamide;

N-(4-chlorobenzyl)-4-hydroxy-8-[(3R)-3-hydroxy-1-butynyl]-6-(4-morpholinylmethyl)-3-cinnolinecarboxamide;

N-(4-chlorobenzyl)-4-hydroxy-6-(4-morpholinylmethyl)-8-{4-[(4R)-2-oxo-1,3-oxazolidin-4-yl]-1-butynyl }-3-cinnolinecarboxamide;

N-(4-chlorobenzyl)-8-[3-(1,1-dioxido-4-thiomorpholinyl)-1-propynyl]-4-hydroxy-6-(4-morpholinylmethyl)-3-cinnolinecarboxamnide;

N-(4-chlorobenzyl)-4-hydroxy-8-(5-hydroxy-1-pentynyl)-6-(4-morpholinylmethyl)-3-cinnolinecarboxamide;

N-(4-chlorobenzyl)-4-hydroxy-8-{[(1R,2S)-2-hydroxycyclopentyl]ethynyl}-6-(4-morpholinylmethyl)-3-cinnolinecarboxamide;

N-(4-chlorobenzyl)-4-hydroxy-8-(3-hydroxy-3-methyl-1-butynyl)-6-(4-morpholinylmethyl)-3-cinnolinecarboxamide;

N-(4-chlorobenzyl)-8-[3-(4,5-dichloro-lH-iHnidazol-1-yl)-1-propynyl]-4-hydroxy-6-(4-morpholinylmethyl)-3-cinnolinecarboxamide;

N-(4-chlorobenzyl)-4-hydroxy-8-(3-hydroxy-1-propynyl)-6-(4-morpholinylmethyl)-3-cinnolinecarboxamide;

N-(4-chlorobenzyl)-8-(cyclopropylethyl)-4-hydroxy-6-(4-morpholinylmethyl)-3-cinnolinecarboxamide;

N-(4-chlorobenzyl)-8-[3-(dimethylamino)-1-propyl]-4-hydroxy-6-(4-morpholinylmethyl)-3-cinnolinecarboxamide;

N-(4-chlorobenzyl)-4-hydroxy-8-(4-hydroxy-1-butyl)-6-(4-morpholinylmethyl)-3-cinnolinecarboxamide;

N-(4-chlorobenzyl)-4-hydroxy-8-[(1-hydroxycyclohexyl)ethyl]-6-(4-morpholinylmethyl)-3-cinnolinecarboxamide;

N-(4-chlorobenzyl)-8-(3,3-dicyclopropyl-3-hydroxy-1-propyl)-4-hydroxy-6-(4-morpholinylmethyl)-3-cinnolinecarboxamide;

N-(4-chlorobenzyl)-4-hydroxy-8-[(3S)-3-hydroxy-1-butyl]-6-(4-morpholinylmethyl)-3-cinnolinecarboxamide;

8-{3-[(aminocarbonyl)amino]-3-methyl-1-butyl}-N-(4-chlorobenzyl)4-hydroxy-6-(4-morpholinylmethyl)-3-cinnolinecarboxamide;

N-(4-chlorobenzyl)-4-hydroxy-8-[3-methyl-3-(4-thioxo-1,3,5-triazinan-1-yl)-1-butyl]-6-(4-morpholinylmethyl)-3-cinnolinecarboxamide;

N-(4-chlorobenzyl)-4-hydroxy-8-[(3R)-3-hydroxy-1-butyl]-6-(4-morpholinylmethyl)-3-cinnolinecarboxamide;

N-(4-chlorobenzyl)-4-hydroxy-6-(4-morpholinylmethyl)-8-{4-[(4R)-2-oxo-1,3-oxazolidin-4-yl]-1-butyl}-3-cinnolinecarboxamide;

N-(4-chlorobenzyl)-8-[3-(1,1-dioxido-4-thiomorpholinyl)-1-propyll-4-hydroxy-6-(4-morpholinylmethyl)-3-cinnolinecarboxamide;

N-(4-chlorobenzyl)-4-hydroxy-8-(5-hydroxy-1-pentynyl)-6-(4-morpholinylmethyl)-3-cinnolinecarboxamnide;

N-(4-chlorobenzyl)-4-hydroxy-8-{[(1R,2S)-2-hydroxycyclopentyl]ethyl}-6-(4-morpholinylmethyl)-3-cinnolinecarboxamide;

N-(4-chlorobenzyl)-4-hydroxy-8-(3-hydroxy-3-methyl-1-butyl)-6-(4-morpholinylmethyl)-3-cinnolinecarboxamide;

N-(4-chlorobenzyl)-8-[3-(4,5-dichloro-1H-imidazol-1-yl)-1-propyl]-4-hydroxy-6-(4-morpholinylmethyl)-3-cinnolinecarboxamide;

N-(4-chlorobenzyl)-4-hydroxy-8-(3-hydroxy-1-propyl)-6-(4-morpholinylmethyl)-3-cinnolinecarboxamide;

N-(4-chlorobenzyl)-4-hydroxy-8-(3-hydroxy-1-propynyl)-3-cinnolinecarboxamide;

N-(4-chlorobenzyl)-4-hydroxy-8-(4-hydroxy-1-butynyl)-3-cinnolinecarboxamide;

N-(4-chlorobenzyl)-4-hydroxy-8-(3-hydroxy-1-propynyl)-6-(tetrahydro-2H-pyran-4-ylmethyl)-3-cinnolinecarboxamide;

N-(4-chlorobenzyl)-4-hydroxy-8-(phenylethynyl)-6-(tetrahydro-2H-pyran-4-ylmethyl)-3-cinnolinecarboxamide;

N-(4-chlorobenzyl)-4-hydroxy-8-(3-hydroxy-3-phenyl-1-propynyl)-6-(tetrahydro-2H-pyran-4-ylmethyl)-3-cinnolinecarboxamide;

N-(4-chlorobenzyl)-4-hydroxy-8-(4-hydroxy-1-butynyl)-6-(tetrahydro-2H-pyran-4-ylmethyl)-3-cinnolinecarboxamide;

N-(4-chlorobenzyl)-8-[3-(dimethylamino)-1-propynyl]-4-hydroxy-6-(tetrahydro-2H-pyran-4-ylmethyl)-3-cinnolinecarboxamide;

N-(4-chlorobenzyl)-4-hydroxy-8-{[(1R,2R)-1-hydroxy-2-methylcyclohexyl]ethynyl}-6-(tetrahydro-2H-pyran-4-ylmethyl)-3-cinnolinecarboxamide;

N-(4-chlorobenzyl)-4-hydroxy-8-{4-[(4R)-2-oxo-1,3-oxazolidin-4-yl]-1-butynyl-}6-(tetrahydro-2H-pyran-4-ylmethyl)-3-cinnolinecarboxamide;

N-(4-chlorobenzyl)-4-hydroxy-8-(3-hydroxy-1-propyl)-6-(tetrahydro-2H-pyran-4-ylmethyl)-3-cinnolinecarboxamide;

N-(4-chlorobenzyl)-4-hydroxy-8-(phenylethyl)-6-(tetrahydro-2H-pyran-4-ylmethyl)-3-cinnolinecarboxamide;

N-(4-chlorobenzyl)4-hydroxy-8-(3-hydroxy-3-phenyl-1-propyl)-6-(tetrahydro-2H-pyran-4-ylmethyl)-3-cinnolinecarboxamide;

N-(4-chlorobenzyl)-4-hydroxy-8-(4-hydroxy-1-butyl)-6-(tetrahydro-2H-pyran-4-ylmethyl)-3-cinnolinecarboxamide;

N-(4-chlorobenzyl)-8-[3-(dimethylamino)-1-propyl]-4-hydroxy-6-(tetrahydro-2H-pyran-4-ylmethyl)-3-cinnolinecarboxamide;

N-(4-chlorobenzyl)-4-hydroxy-8-{[(1R,2R)-1-hydroxy-2-methylcyclohexyl]ethyl}-6-(tetrahydro-2H-pyran-4-ylmethyl)-3-cinnolinecarboxamide; and N-(4-chlorobenzyl)-4-hydroxy-8-{4-[(4R)-2-oxo-1,3-oxazolidin-4-yl]-1-butyl}-6-(tetrahydro-2H-pyran-4-ylmethyl)-3-cinnolinecarboxamide.

The following Charts A–I describe the preparation of the compounds of the present invention. All of the starting materials and final compounds are prepared by procedures described in these charts or by procedures analogous thereto, which would be well known to one of ordinary skill in organic chemistry. All of the variables used in the charts are as defined below or as in the claims.

The general ring system can be prepared in several ways. An example of the first route is shown in Chart A. Carboxylation of 4-fluoro-1-iodobenzene by treatment with a base such as lithium diisopropylamide followed by quenching with $CO_2$ provides the alpha-fluorocarboxylic acid A-2. This can be elaborated to the beta-ketoester by activation of the acid and displacement with the TMS ester of ethyl malonate. Diazotization, reduction and cyclization provides the 4-hydroxycinnoline-3-carboxylic ester (*Chem Pharm Bull*, 1988, 38, 1321). Treatment with an amine such as 4-chlorobenzylamine at elevated temperature provides the 4-hydroxycinnoline-3-carboxamide.

Chart A

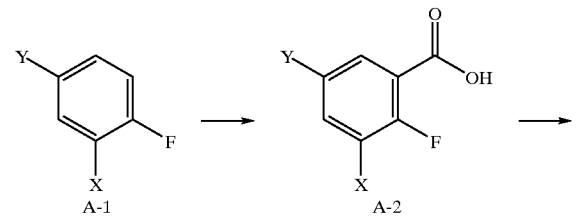

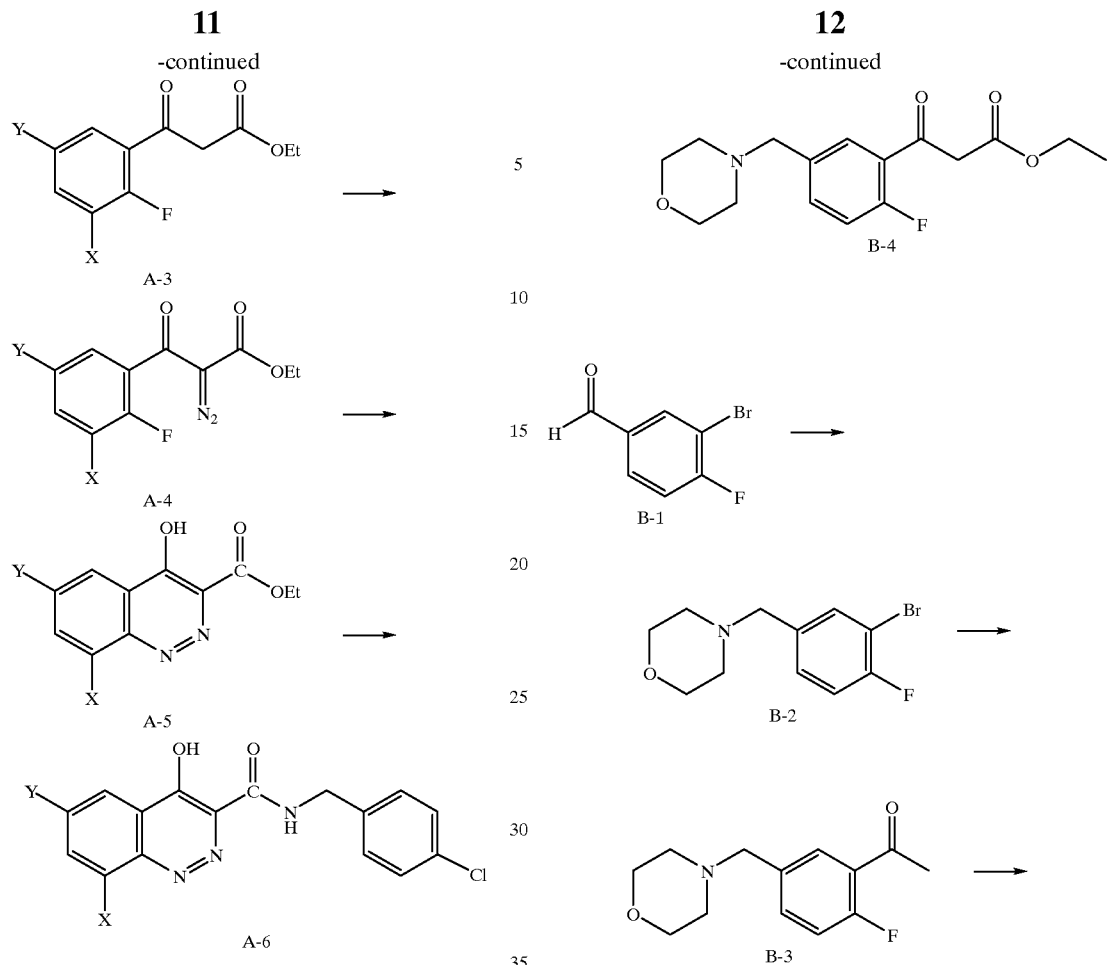

The requisite beta-ketoesters can be prepared by several different methods, one of which is shown in Chart B. Reductive amination of 3-bromo-4-fluorobenzaldehyde with an amine such as morpholine provides the substituted benzene B-2. Metallation with n-BuLi and trapping N-methoxy-N-methylacetamide will give the ketone B-3 which can be elaborated to the beta-ketoester by treatment with sodium hydride and diethyl carbonate.

CHART B

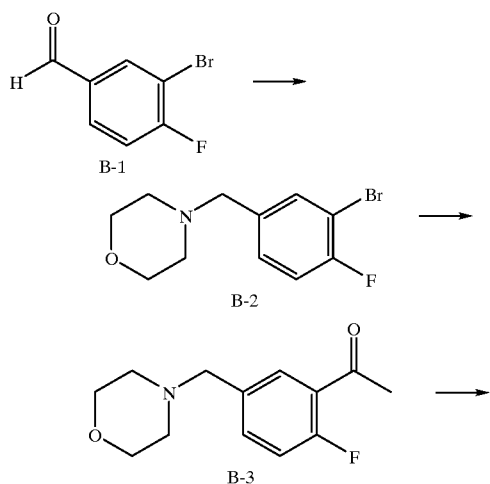

Alternatively, the fluorobenzene C-2 can be directly lithiated with lithium diisopropylamide. Trapping of the resulting anion with an electrophile such as iodine followed by a subsequent deprotonation and trapping with $CO_2$ will provide the disubstituted acid C-4. This again can be elaborated to the beta-ketoester by activation of the acid with a condensing agent such as 1,1'-carbonyldiimidazole and displacement with the TMS ester of ethyl malonate.

CHART C

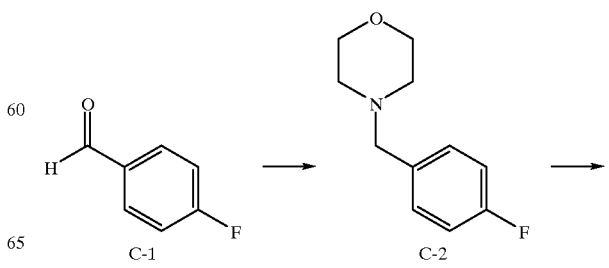

-continued

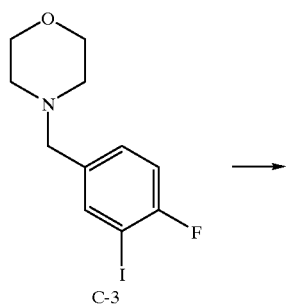
C-3

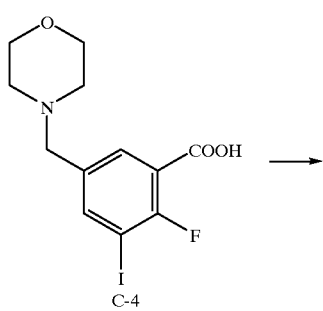
C-4

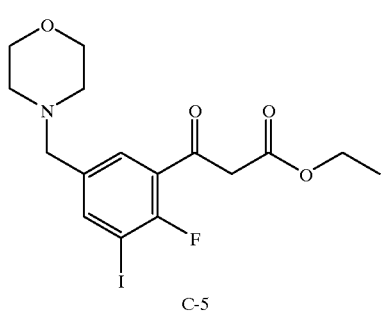
C-5

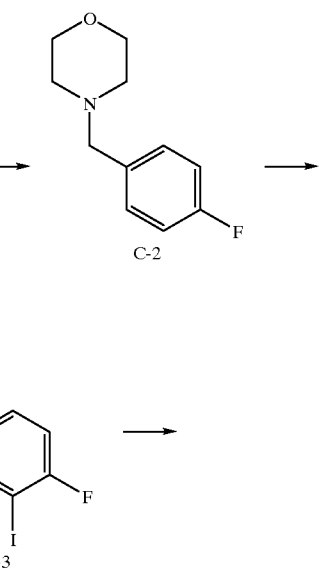
C-1
C-2
C-3

-continued

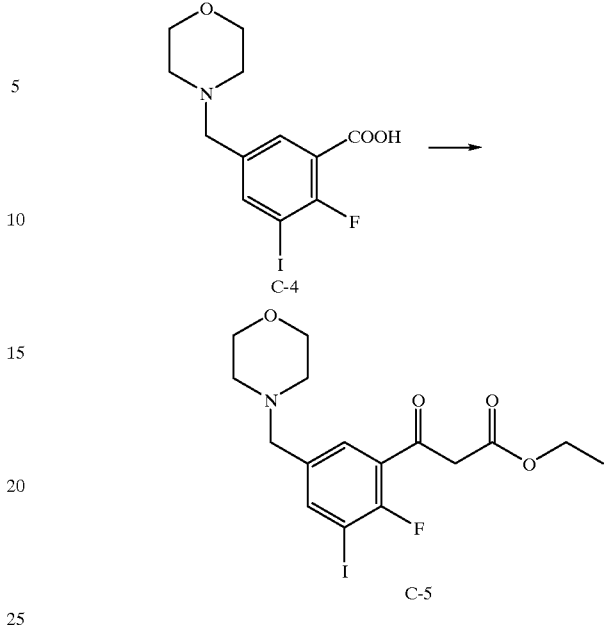
C-4
C-5

The cinnoline ring system can also be prepared as shown in Chart D. Diazotization of an aniline followed by treatment with diethyl malonate provides the cyclization precursor. Cyclization is then effected by hydrolysis to the diacid, treatment with thionyl chloride to form the diacid chloride and cyclization promoted by TiCl$_4$ (J. Chem. Soc. 1961, 2828–2843). The resulting cinnoline 3-carboxylic acid can then be condensed with an amine such as 4-chlorobenzylamine by activation of the acid with a condensing agent such as 1,1'-carbonyldiimidazole and subsequent coupling of the activated acid with the desired amine.

CHART D

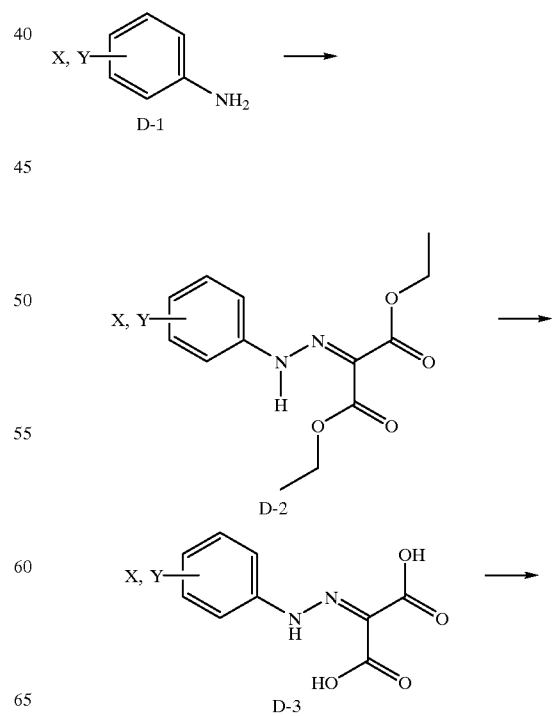
D-1
D-2
D-3

-continued

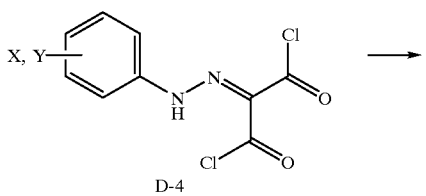

D-4

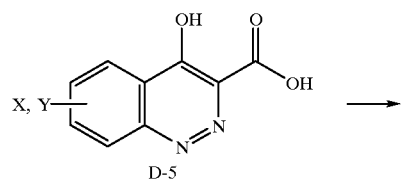

D-5

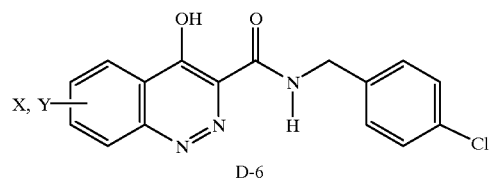

D-6

The requisite anilines for the above synthesis can be obtained from commercial sources, prepared according to literature procedures or further functionalized, an example of which is shown in Chart E. Iodination of the aniline can be accomplished by treatment with an appropriate iodinating agent, such as ICl.

CHART E

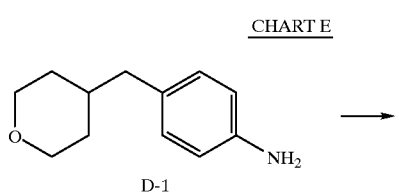

D-1

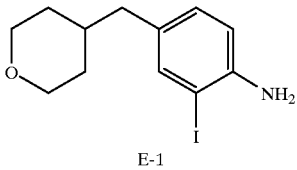

E-1

The cinnolines can be further elaborated. One such elaboration is a palladium-catalyzed coupling of compounds such as A-1 where Y=I with acetylenes such as propargyl alcohol shown in Chart F.

CHART F

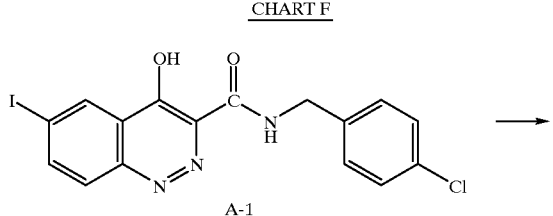

A-1

-continued

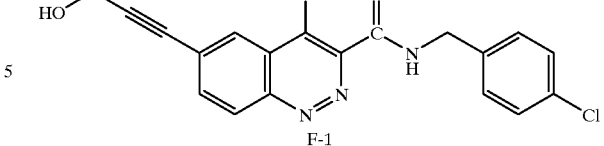

F-1

A second example of elaboration of the cinnoline substitution is the preparation of the hydroxymethyl substituted cinnoline shown in Chart G. Palladium catalyzed carbomethylation of the cinnoline ring system (A-1 where Y=I) provides the methyl ester G-1. Reduction of the ester provides the 6-hydroxymethyl substituted cinnoline.

CHART G

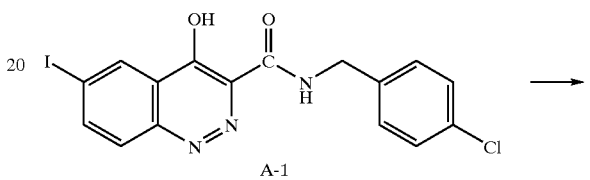

A-1

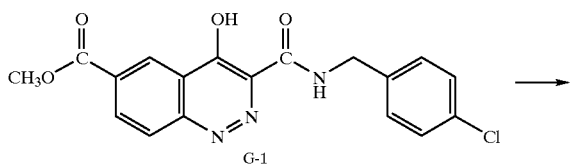

G-1

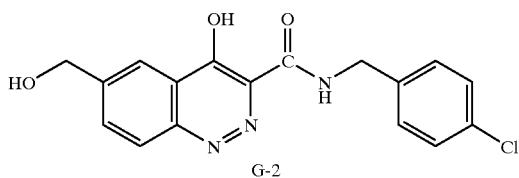

G-2

Alcohols such as the one depicted in Chart G can be further elaborated as shown in Chart H by activation with reagents such as methanesulfonyl chloride and displacement with nucleophiles such as thiols or amines (e.g. morpholine).

CHART H

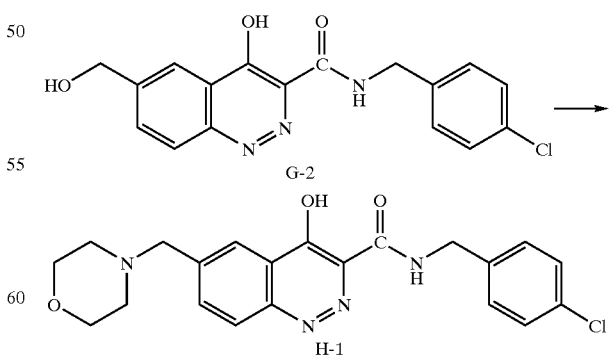

G-2

H-1

The cinnolines prepared as in Charts A or D can be further elaborated. One example of such an elaboration is shown in Chart I. Compound A-1 (where X=morpholinylmethyl and Y=I) can undergo palladium-catalyzed coupling with acetylenes to produce compounds such as I-1. Hydrogenation with an appropriate catalyst such as palladium on carbon would provide compounds such as 1–2.

CHART I

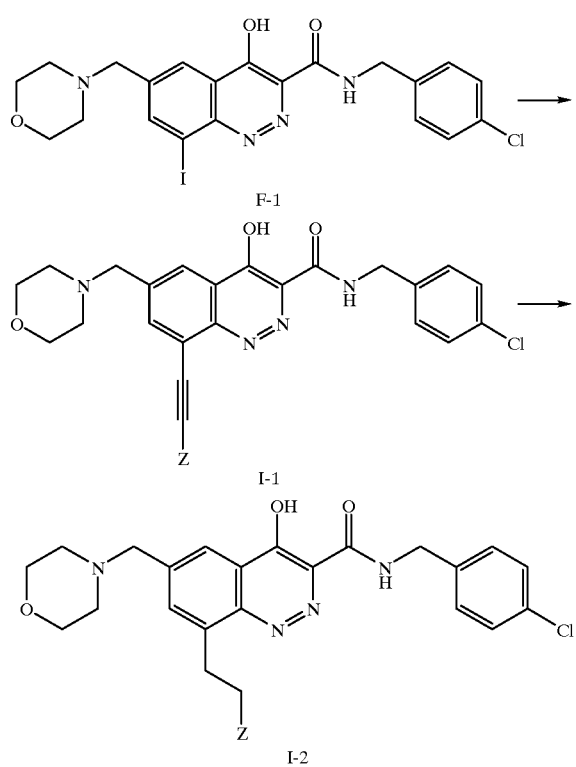

The inventive compounds may be used in their native form or as salts. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient, the composition being useful in combating viral infections. Pharmaceutical compositions containing a compound appropriate for antiviral use are prepared by methods and contain excipients which are well known in the art. A generally recognized compendium of such methods and ingredients is Remington's Pharmaceutical Sciences by E. W. Martin (Mark Publ. Co., 15th Ed., 1975). To the extent necessary for completion, this publication is expressly incorporated by reference. The compounds and compositions of the present invention can be administered parenterally (for example, by intravenous, intraperitoneal or intramuscular injection), topically, intravaginally, intranasally, orally, or rectally, depending on whether the preparation is used to treat internal or external viral infections.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, cyclodextrins, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula II to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula II can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing 5 to 1000 mg, conveniently 10 to 750 mg, most conveniently, 50 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

For internal infections, the compositions can be administered orally or parenterally at dose levels, calculated as the free base, of about 0.1 to 300 mg/kg, preferably 1.0 to 30 mg/kg of mammal body weight, and can be used in man in a unit dosage form, administered one to four times daily in the amount of 1 to 1000 mg per unit dose.

For parenteral administration or for administration as drops, as for eye infections, the compounds are presented in aqueous solution in a concentration of from about 0.1 to about 10%, more preferably about 0.1 to about 7%. The solution may contain other ingredients, such as emulsifiers, antioxidants or buffers.

Generally, the concentration of the compound(s) of formula II in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The exact regimen for administration of the compounds and compositions disclosed herein will necessarily be dependent upon the needs of the individual subject being treated, the type of treatment and, of course, the judgment of the attending practitioner. The compounds of the present invention can be administered to an animal in need of treatment. In most instances, this will be a human being, but the treatment of livestock (e.g. food animals such as cows, pigs, goats, sheep, deer, etc.) and companion animals (e.g. dogs, cats, fish, horses and birds) is also specifically contemplated as falling within the scope of the instant invention.

The invention will be further described by the following non-limiting examples.

COMPARATIVE EXAMPLE 1

PNU-170714

N-(4-chlorobenzyl)-4-oxo-1,4-dihydro-3-cinnolinecarboxamide

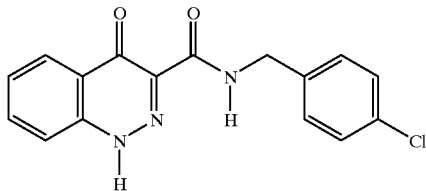

4-Oxo-1,4-dihydro-3-cinnolinecarboxylic acid (0.10 g, 0.53 mmol) is dissolved in 5 mL DMF. To this is added 4-chlorobenzylamine (0.07 ML, 0.58 mmol) and the reaction mixture is stirred at room temperature for 5 min. EDC (0.11 g, 0.57 mmol) and HOBt (0.08 g, 0.56 mmol) are added and the reaction is stirred at room temperature over 2 days. The mixture is poured into 30 mL H$_2$O. A brown precipitate formed which is filtered. The crude product is triturated with hot EtOAc, filtered and dried to yield 0.012 g (7%) of the desired product. Physical characteristics are as follows: m.p. 269–271° C.; $^1$H NMR (300 MHz, DMSO) δ 14.2, 10.0, 8.17, 7.87, 7.74, 7.56, 7.38, 4.53; MS (fab) m/z 314 (M+H)$^+$, 316, 315, 299, 298, 297, 127, 125, 123, 58.

Preparation 1

PNU-244019

2-fluoro-5-iodobenzoic acid

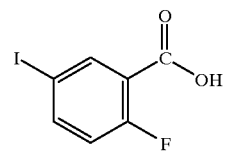

To a −78° C. solution of iPr$_2$NH (16.80 mL, 0.12 mol) in 200 mL freshly distilled THF is added n-butyllithium (68 mL, 0.11 mol) dropwise, maintaining the temperature of the reaction below −65° C. The reaction is stirred for 10 minutes, then 1-fluoro-4-iodobenzene (11.50 mL, 0.10 mol) as a solution in 10 mL THF is added over 20 minutes. The reaction is stirred at −78° C. for 90 minutes, then cannulated rapidly into diethyl ether (180 mnL) and dry ice (approximately 75 g). The reaction is stirred at room temperature overnight. To the ether solution is added 1N NaOH (100 mL) and water (200 mL) and the solution placed in a separatory funnel. The aqueous layer is removed. The organic layer is washed with $H_2O$ (2×100 mL). All the aqueous portions are combined, chilled in ice/$H_2O$, and acidified to pH 2 with 6N HCl. This solution is then extracted with diethyl ether (2×200 mL). The ether portions are combined, dried over $Na_2SO_4$, filtered, and concentrated to give a pale yellow solid. The solid is dissolved in a minimal amount of EtOAc on the steam bath, and hexanes are added to affect recrystallization. After standing in the freezer overnight, the product is obtained as a crystalline white solid (15.44 g, 0.058 mol, 58%). Physical characteristics are as follows: m.p. 157–159° C.; $^1$H NMR (300 MHz, $CDCl_3$) δ 8.34, 7.88, 6.97; IR (drift) 3098, 3079, 3051, 3017, 3007, 2998, 2981, 2971, 2881, 2817, 1708, 1681, 1300, 1236, 824 $cm^{-1}$; Anal. Calcd for $C_7H_4FIO_2$: C, 31.61; H, 1.52; Found: C, 31.70; H, 1.59.

Preparation 2

PNU-244020

Ethyl 3-(2-fluoro-5-iodophenyl)-3-oxopropanoate

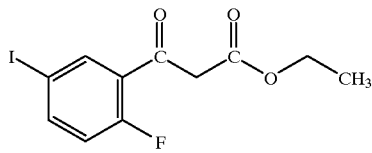

To a solution of 2-fluoro-5-iodobenzoic acid (4.03 g, 15.14 mmol) in 11 mL freshly distilled THF is added CDl (2.96 g, 18.24 mmol) in small portions. Vigorous gas evolution is observed. The reaction is stirred overnight. In a separate flask, ethyl malonate potassium salt (2.84 g, 16.69 mmol) is suspended in 10 mL $CH_3CN$. To this solution is added chlorotrimethylsilane (2.15 mL, 16.94 mmol) and the reaction is stirred at room temperature overnight. The latter reaction is cooled to 0° C. and DBU (5.00 mL, 33.43 mmol) is added dropwise. This reaction is stirred at 0° C. for 3 h. The solution of the CDI adduct is then cannulated over and the mixture is stirred at 0° C. for 2 h. Upon complete conversion to product as evidenced by TLC, the solution is quenched with water and 6N HCl (8 mL). The reaction is partitioned with diethyl ether. The organic layer is washed with 1N HCl and then brine, dried over $Na_2SO_4$, filtered, and concentrated to give a light orange oil. The oil is dissolved in EtOAc and adsorbed onto silica. Purification by chromatography (eluent 3% EtOAc/hexanes) affords the desired product as a colorless oil which crystallized upon standing (2.51 g, 7.46 mmol, 49%). Physical characteristics are as follows: m.p. 54–56° C.; $^1$H NMR (300 MHz, $CDCl_3$) δ 12.67, 8.18, 7.70, 6.89, 5.54, 4.28, 1.35; IR (drift) 2984, 1627, 1558, 1476, 1422, 1390, 1358, 1292, 1262, 1221, 1201, 1071, 1028, 823, 807 cm$^{-1}$; MS (EI) m/z 336 ($M^+$), 336, 249, 122, 107, 94, 86, 84, 69, 68, 51; Anal. Calcd for $C_{11}H_{10}FIO_3$: C, 39.31; H, 3.00; Found: C, 39.35; H, 2.92.

Preparation 3

PNU-2445037

Ethyl 4-hydroxy-6-iodo-3-cinnolinecarboxylate

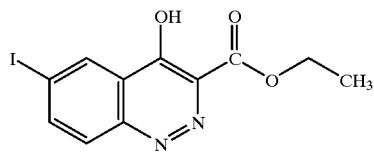

A solution of tosyl azide (0.69 g, 3.50 mmol, prepared according to Org. Prep. Proc. Intl., 1981, 13, 112.) in $CH_3CN$ (2 mL) is added in one portion to a solution of ethyl 3-(2-fluoro-5-iodophenyl)-3-oxopropanoate (1.01 g, 3.01 mmol) and $NEt_3$ (0.47 mL, 3.37 mmol) in $CH_3CN$ (10 niL) cooled below 10° C. in an ice/water bath. The reaction is stirred for 15 minutes at this temperature, then at room temperature for 2 h. The reaction is concentrated in vacuo keeping the temperature of the rotary evaporator bath below 50° C. The residue is cooled in an ice bath and 2N NaOH was added. The aqueous solution is extracted with $CHCl_3$ (2×200 mL). The organic portions are combined, washed with water, then dried over $Na_2SO_4$, filtered, and concentrated in vacuo to give a yellow oil. The oil is purified by chromatography (eluent $CH_2Cl_2$ (lL)) to give the intermediate diazo compound as a pale yellow oil (1.20 g, 3.33 mmol, quant.). Physical characteristics are as follows: $^1$H NMR (300 MHz, $CDCl_3$) δ 7.75, 6.87, 4.24, 1.24;

To a solution of the diazo compound (1.11 g, 3.07 mmol) in 12 mL isopropyl ether is added tributylphosphine (0.86 nmL, 3.44 mmol) as a solution in 4 mnL isopropyl ether. The reaction is stirred at room temperature for 30 minutes, then refluxed for 5 h. The reaction is cooled to room temperature and the resulting yellow solid is filtered and dried. The solid is dissolved in $CH_2Cl_2$/MeOH and adsorbed onto silica. Purification by chromatography (eluent 1% MeOH/$CH_2Cl_2$ (1 L), 2% MeOH/$CH_2Cl_2$ (1 L), 4% MeOH/$CH_2Cl_2$ (1 L), 5% MeOH/$CH_2Cl_2$ (1 L)) affords the desired product as a yellow solid (0.22 g, 0.64 mmol, 21%). Physical characteristics are as follows: m.p. 242–244° C.; $^1$H NMR (300 MHz, DMSO-$d_6$) δ 14.00, 8.38, 8.13, 7.49, 4.30, 1.30; IR (drift) 3164, 3128, 3093, 1700, 1621, 1518, 1455, 1373, 1348, 1297, 1224, 1198, 1121, 824, 802 $cm^{-1}$; MS (EI) m/z 344 ($M^+$), 272, 120, 92, 91, 89, 86, 84, 73, 63, 58; HRMS (FAB) calcd for $C_{11}H_9IN_2O_3+H_1$ 344.9738, found 344.9739.

COMPARATIVE EXAMPLE 2

PNU-247198

N-(4-chlorobenzyl)-4-hydroxy-6-iodo-3-cinnolinecarboxamide

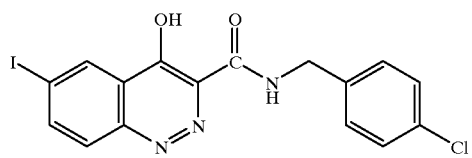

A solution of ethyl 4-hydroxy-6-iodo-3-cinnolinecarboxylate (0.27 g, 0.79 mmol) and 4-chlorobenzylamine (3.50 mL, 28.77 mmol) is heated at 90° C. for 30 minutes. The reaction is cooled slightly and poured into 25 mL EtOAc. Hexanes are added to precipitate the product and the resulting solid is filtered and dried. The product is further purified by trituration with $CH_2Cl_2$/hexanes (0.29 g, 0.67 nmmol, 85%). Physical characteristics

EXAMPLE 3

PNU-251095

Methyl 3-{[(4-chlorobenzyl)amino]carbonyl]-4-hydroxy-6-cinnolinecarboxylate

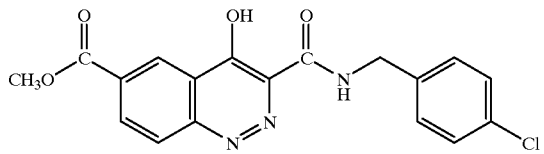

A flame-dried flask is charged with N-(4-chlorobenzyl)-4-hydroxy-6-iodo-3-cinnolinecarboxamide (0.23 g, 0.52 mmol), NEt$_3$ (0.15 mL, 1.08 mmol), Pd(PPh$_3$)$_2$Cl$_2$ (0.071 g, 0.10 mmol), methanol (0.85 mL, 20.98 mmol), and anhydrous DMF (5 mL). The reaction is placed under a CO balloon atmosphere and heated at 70° C. for 5 h at which point TLC shows disappearance of starting material. The reaction is cooled to room temperature and poured into 40 mL 1N HCl. The resulting solid is filtered and dried. The crude solid is dissolved in CH$_2$Cl$_2$/MeOH and adsorbed onto silica. Purification by chromatography (eluent 1% MeOH/CH$_2$Cl$_2$ (1 L), 1.5% MeOH/CH$_2$Cl$_2$ (1 L), 2% MeOH/CH$_2$Cl$_2$ (3L), 3% MeOH/CH$_2$Cl$_2$ (1 L)) affords the desired product as an off-white solid (0.12 g, 0.33 mmol, 64%). Physical characteristics are as follows: m.p. 308–310° C.; $^1$H NMR (300 MHz, DMSO-d$_6$) δ 14.37, 9.80, 8.72, 8.34, 7.83, 7.41, 4.55, 3.92; IR (drift) 1725, 1661, 1625, 1600, 1581, 1535, 1486, 1296, 1276, 1245, 1237, 1129, 823, 806, 761 cm$^{-1}$; MS (EI) m/z 371 (M$^+$), 142, 141, 140, 139, 125, 89, 88, 74, 73, 51; HRMS (FAB) calcd for C$_{18}$H$_{14}$ClN$_3$O$_4$+H$_1$ 372.0751, found 372.0757.

EXAMPLE 4

PNU-256719

N-(4-chlorobenzyl)-4-hydroxy-6-(hydroxymethyl)-3-cinnolinecarboxamide

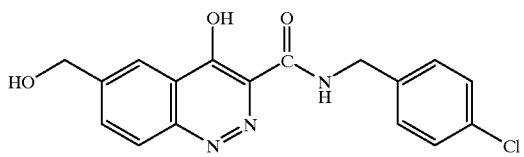

To a suspension of methyl 3-{[(4-chlorobenzyl)amino]carbonyl}-4-hydroxy-6-cinnolinecarboxylate (0.48 g, 1.29 mmol) in 40 mL THF is added lithium aluminum hydride (2.60 mL, 2.60 mmol) dropwise. The reaction turns a dark green color. After 1 h, the reaction is quenched carefully with water, 15% NaOH, and water again. The reaction is filtered to remove aluminum salts. The filtrate is concentrated and the resulting residue is dissolved in CH$_2$Cl$_2$/MeOH and adsorbed onto silica. Purification by chromatography (eluent CH$_2$Cl$_2$ (1 L), 0.5% MeOH/CH$_2$Cl$_2$ (1 L), 1% MeOH/CH$_2$Cl$_2$ (1 L), 2% MeOH/CH$_2$Cl$_2$ (1 L), 3% MeOH/CH$_2$Cl$_2$ (1 L), 4% MeOH/CH$_2$Cl$_2$ (1 L), 5% MeOH/CH$_2$Cl$_2$ (2 L), 5.5% MeOH/CH$_2$Cl$_2$ (2L)) affords the desired product (0.23 g, 0.67 mmol, 52%). Physical characteristics are as follows: m.p. 296–298° C.; $^1$H NMR (300 MHz, DMSO-d$_6$) δ 10.12, 8.14, 7.84, 7.74, 7.41, 5.50, 4.66, 4.56; IR (drift) 2922, 2873, 1647, 1602, 1555, 1490, 1358, 1183, 1022, 930, 919, 836, 808, 722, 684 cm$^{-1}$; MS (FAB) m/z 344 (MH$^+$), 346, 344, 287, 229, 153, 133, 125, 121, 107, 103; HRMS (FAB) calcd for C$_{17}$H$_{14}$ClN$_3$O$_3$+H$_1$ 344.0802, found 344.0805.

Preparation 4

4-(3-Bromo-4-fluorobenzyl)morpholine

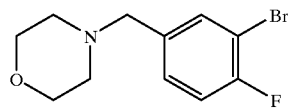

A solution of 3-bromo-4-fluorobenzaldehyde (50.0 g) in 1,2-dichloroethane (500 mL) is cooled to 0° C. Acetic acid (14.1 mL) and morpholine (23.6 mL) are added slowly, maintaining the temperarture below 4° C. Sodium triacetoxyborohydride (78.3 g) is added all at once, maintaining the temperature below 5° C. The mixture is allowed to warm to rt and stirred for 18 hrs. The reaction is quenched with 1 N NaOH (200 mL) and extracted with CH$_2$Cl$_2$ (500 mL). The organic layer is washed with 1 N NaOH (2×200 mL). The aqueous layers are combined and back-extracted with CH$_2$Cl$_2$ (100 mL). The organic layers are combined and extracted with 0.5 N HCl (5×250 mL). The acidic aqueous layers are combined, and 2 N NaOH is added until the solution is basic (pH=12). The aqueous layer is then extracted with CH$_2$Cl$_2$ (6×100 mL). The organic layers are combined, dried (MgSO$_4$) and concentrated in vacuo to a clear, colorless oil. The crude product is distilled (126° C., 0.3 Torr) to afford 48.9 g (72%) of the title compound as a clear, colorless oil. Physical characteristics: Bp 126° C. (0.3 Torr); $^1$H NMR (300 MHz, DMSO-d$_6$) δ 7.62, 7.35–7.29, 3.56, 3.45, 2.34; $^{13}$C NMR (75 MHz, DMSO-d$_6$) δ 157.3, 136.1, 133.3, 129.8, 116.2, 107.7, 66.1, 60.9, 53.0; IR (liq.) 2855, 2807, 1495, 1455, 1348, 1257, 1244, 1118, 1009, 862 cm$^{-1}$; MS (ESI+) m/z 274 (M+H)$^+$. Anal. Calcd for C$_{11}$H$_{13}$BrFNO: C, 48.20; H, 4.78; N, 5.11; Br, 29.15. Found: C, 48.04; H, 4.79; N, 5.11; Br, 28.18.

Preparation 5

1-(2-Fluoro-5-(4-morpholinylmethyl)phenyl)ethanone

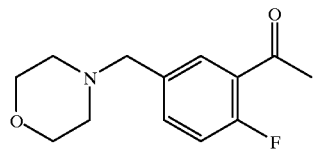

4-(3-Bromo-4-fluorobenzyl)morpholine (Preparation 4, 35.5 g) is dissolved in THF (400 mL) and cooled to −75° C. A solution of n-butyllithium in hexane (2.5 M, 57.0 mL) is added via addition funnel, maintaining the temperature below −68° C. A solution of N-methoxy-N-methylacetamide (16.0 g) in THF (50 mL) is added via addition funnel, maintaining the temperature below −65° C. The reaction is stirred at −75° C. for 1 h and allowed to warm to rt overnight. The reaction is quenched with 1 N HCl (150 mL)

(top of page, continuation of Example 2):
are as follows: m.p. 307–308° C.; $^1$H NMR (300 MHz, DMSO-d$_6$) δ 9.99, 8.47, 8.15, 7.57, 7.40, 4.55; IR (drift) 2972, 2958, 2901, 2846, 1645, 1601, 1557, 1488, 1458, 1356, 933, 922, 822, 806, 722 cm$^{-1}$; MS (ESI) m/z 439.8 (M+H)$^+$, 437.8 (M—H)$^-$; Anal. Calcd for C$_{16}$H$_{11}$ClIN$_3$O$_2$: C, 43.71; H, 2.52; N, 9.56; Found: C, 43.94; H, 2.50; N, 9.43.

and poured into ethyl acetate (400 mL). The aqueous layer is separated, basified with sat. aq. NaHCO$_3$, and extracted with ethyl acetate (2×100 mL). The combined organic layers are washed with sat. NaHCO$_3$ (2×100 mL) and brine (50 mL). The combined aqueous washes are back-extracted with ethyl acetate (100 mL). The organic layers are combined, dried (Na$_2$SO$_4$), and concentrated in vacuo to a yellow oil. The crude product is distilled (135° C., 0.3 Torr) to afford 19.7 g (64%) of the title compound as a clear, colorless oil. Physical characteristics: Bp 135° C. (0.3 Torr); $^1$H NMR (300 MHz, DMSO-d$_6$) δ 7.72, 7.61–7.56, 7.31, 3.56, 3.48, 2.58, 2.34; IR (liq.) 1996, 1979, 1919, 1688, 1612, 1492, 1417, 1361, 1291, 1281, 1212, 1118, 865 cm$^-$; MS (ESI+) m/z 238 (M+H)$^+$. Anal. Calcd for C$_{13}$H$_{16}$FNO$_2$: C, 65.81; H, 6.80; N, 5.90. Found: C, 65.43; H, 6.75; N, 5.84.

Preparation 6

Ethyl 3-(2-fluoro-5-(4-morpholinylmethyl)phenyl)-3-oxopropanoate

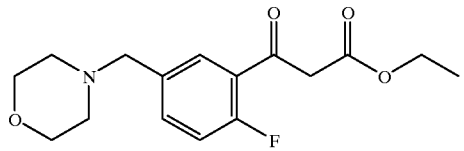

Sodium hydride (60% dispersion in mineral oil, 6.6 g) is slowly added to a solution of 1-(2-fluoro-5-(4-morpholinylmethyl)phenyl)ethanone (Preparation 5, 19.6 g) in diethyl carbonate at 0° C. The mixture is stirred at 0° C. for 1 h and allowed to warm to rt overnight. The reaction is quenched with acetic acid (10 mL), diluted with water (200 mnL) and made basic with sat. aq. Na$_2$CO$_3$. The mixture is extracted with diethyl ether (3 ×200 mL). The combined organic layers are washed with sat. NaHCO$_3$ (100 mL) and brine (50 mL). The combined aqueous layers are back-extracted with diethyl ether (50 mL). The organic layers are combined, dried (Na$_2$SO$_4$) and concentrated in vacuo to an orange oil. The crude product is purified by column chromatography (heptane/IPA, 8/1; 4/1; CH$_2$Cl$_2$/MeOH, 98/2) to afford 20.2 g (79%) of the compound as a yellow oil. Physical characteristics: $^1$H NMR (300 MHz, DMSO-d$_6$) δ 7.78, 7.65–7.60, 7.32, 4.10, 4.05, 3.57, 3.50, 2.34, 1.16; IR (liq.) 1996, 1979, 1744, 1689, 1626, 1611, 1493, 1331, 1260, 1215, 1147, 1117, 865 cm$^{-1}$; MS (ESI+) m/z 310 (M+H)$^+$. Anal. Calcd for C$_{16}$H$_{20}$FNO$_4$: C, 62.12; H, 6.52; N, 4.53. Found: C, 61.96; H, 6.67; N, 4.44.

Preparation 7

Ethyl 2-diazo-3-[2-fluoro-5-(4-morpholinylmethyl)phenyl]-3-oxopropanoate

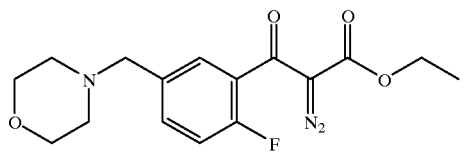

To a solution of ethyl 3-(2-fluoro-5-(4-morpholinylmethyl)phenyl)-3-oxopropanoate (Preparation 6, 5.00 g) and triethylamine (2.48 mL) in 50 mL CH$_3$CN cooled to 0° C. is added toluenesulfonyl azide (3.51g, prepared according to *Org. Prep. Proc. Intl.*, 1981, 13, 112) in 10 mL CH$_3$CN. The reaction is stirred at 0° C. for 15 mnin then at room temperature for 2 h. The reaction is concentrated (below 50° C.). 2N NaOH (25 mL) is added. The aqueous layer is extracted with CHCl$_3$ (3×). The combined organic layers are washed, dried and concentrated to yield 4.68 g (86%) of the desired product as a yellow oil. Physical characteristics are as follows: $^1$H NMR (CDCl$_3$) δ 7.52, 7.44, 7.06, 4.24, 3.75, 3.55, 2.50, 1.24; MS (ESI+) for C$_{16}$HI$_8$FN$_3$0$_4$ m/z 336.1 (M+H)$^+$.

Preparation 8

Ethyl 4-hydroxy-6-(4-morpholinylmethyl)-3-cinnolinecarboxylate

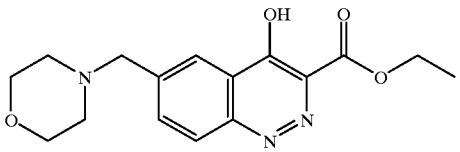

A solution of Bu$_3$P (3.90 iL) in dioxane (20 mL) is added to a stirred solution of ethyl 2-diazo-3-[2-fluoro-5-(4-morpholinylmethyl)phenyl]-3-oxopropanoate (Preparation 7, 3.16 g) in dry dioxane (56 mL). The mixture is stirred at room temperature for 30 min then gently refluxed for 1.5 h. The reaction is cooled and concentrated. The crude product is purified by column chromatography (CH$_2$Cl$_2$/MeOH, 99/1; CH$_2$Cl$_2$/MeOH, 98/2; CH$_2$Cl$_2$/MeOH, 95/5) to yield 0.200 g (4.5%) of the desired product as an off-white solid. Additional material can be obtained by heating the acyclic intermediate which was isolated in the chromatography at 130° C. in diglyme (32 mL) for 3.5 h. The resulting mixture is concentrated. The crude product is purified by column chromatography (CH$_2$Cl$_2$/MeOH, 99/1; CH$_2$Cl$_2$/MeOH, 98/2; CH$_2$Cl$_2$/MeOH, 95/5) to yield 0.531 g (30% %) of the desired product as a white solid to give an overall yield of 0.731 g (35%). Physical characteristics are as follows: m.p. 195–197° C. (dec); $^1$H NMR (DMSO-d$_6$) δ 14.0, 8.01, 7.83, 7.67, 4.30, 3.60, 2.38, 1.30; MS (ESI-) for C$_{16}$H$_{19}$N$_3$O$_4$ m/z 316.1 (M—H)$^-$.

EXAMPLE 5

N-(4-chlorobenzyl)-4-hydroxy-6-(morpholinylmethyl)-3-cinnolinecarboxylate

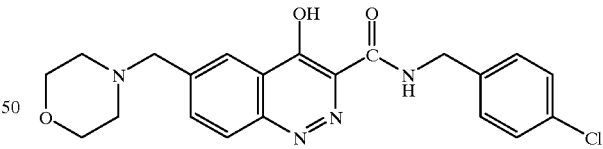

A solution of ethyl 4-hydroxy-6-(4-morpholinylmethyl)-3-cinnolinecarboxylate (Preparation 8, 0.382 g) and 4-chlorobenzylamine (1.46 miL) is heated to 80° C. for 30 min over which time a solid forms. The reaction is diluted with Et$_2$O and the resulting solid is collected and dried to yield 0.443 g (89%) of the desired compound as an off-white solid. Physical characteristics are as follows: m.p. 277–280° C. (dec); $^1$H NMR (DMSO-d$_6$) δ 10.12, 8.09, 7.86, 7.74, 7.40, 4.56, 3.63, 3.58, 2.38; MS (ESI+) for C$_{21}$H$_{21}$ClN$_4$O$_3$ m/z 413.0 (M+H)$^+$ MS (ESI-), 410.9 (M—H)$^-$.

Testing of Inventive Compounds

The antiviral activity of a compound of the invention can be determined using pharmacological models which are well known to the art, or using Test A described below.

The compounds of formula (II) and pharmaceutically acceptable salts thereof are useful as antiviral agents. Thus, they are useful to combat viral infections in animals, including man. The compounds are generally active against herpes viruses, and are particularly useful against the varicella zoster virus (ZVZ), the Epstein-Barr virus, the herpes simplex virus, the human herpes virus type 8 (HHV-8) and the cytomegalovirus (CMV).

While many of the compounds of the present invention have shown activity against the CMV polymerase, these compounds may be active against the cytomegalovirus by this or other mechanisms of action. Thus, the description below of these compounds' activity against the CMV polymerase is not meant to limit the present invention to a specific mechanism of action.

Test A

The HCMV polymerase assay is performed using a scintillation proximity assay (SPA) as described in several references, such as N. D. Cook, et al., Pharmaceutical Manufacturing International, pages 49–53 (1992); K. Takeuchi, Laboratory Practice, September issue (1992); U.S. Pat. No. 4,568,649 (1986); which are incorporated by reference herein. Reactions are performed in 96-well plates. The assay is conducted in 100 μl volume with 5.4 mM HEPES (pH 7.5), 11.7 mM KCl, 4.5 mM $MgCl_2$, 0.36 mg/ml BSA, and 90 nM $^3$H-dTTP. Assays are run with and without CHAPS, (3-[(3-cholamidopropyl)-dimethylammonio]-1-propane-sulfonate) at a final concentration of 2 mM. HCMV polymerase is diluted in enzyme dilution buffer containing 50% glycerol, 250 mM NaCl, 10 mM HEPES (pH 7.5), 100 μg/ml BSA, and 0.01% sodium azide. The HCMV polymerase, which is expressed in recombinant baculovirus-infected SF-9 cells and purified according to literature procedures, is added at 10% (or 10 μl) of the final reaction volume, i.e., 100 μl. Compounds are diluted in 50% DMSO and 10 μl are added to each well. Control wells contain an equivalent concentration of DMSO. Unless noted otherwise, reactions are initiated via the addition of 6 nM biotinylated poly(dA)-oligo(dT) template/primer to reaction mixtures containing the enzyme, substrate, and compounds of interest. Plates are incubated in a 25° C. or 37° C. $H_2O$ bath and terminated via the addition of 40 μl/reaction of 0.5 M EDTA (pH 8) per well. Reactions are terminated within the timeframe during which substrate incorporation is linear and varied depending upon the enzyme and conditions used, i.e., 30 min. for HCMV polymerase. Ten μl of streptavidin-SPA beads (20 mg/ml in PBS/10% glycerol) are added following termination of the reaction. Plates are incubated 10 min. at 37° C., then equilibrated to room temperature, and counted on a Packard Topcount. Linear regressions are performed and $IC_{50}$'s are calculated using computer software.

A modified version of the above HCMV polymerase assay is performed as described above, but with the following changes: Compounds are diluted in 100% DMSO until final dilution into assay buffer. In the previous assay, compounds are diluted in 50% DMSO. 4.5 mM dithiotherotol (DTT) is added to the polymerase buffer. Also, a different lot of CMV polymerase is used, which appears to be more active resulting in a more rapid polymerase reaction. Results of the testing of representative compounds of formula II in this assay are shown in Table 1. All results are listed as the percent inhibition of the viral polymerase at a concentration of 20 μM. In Table 1, the term "nd" refers to activity data not determined.

| Example | HCMV | HSV | VZV |
|---|---|---|---|
| Comp. 1 | 90 | 20.8 | 10.1 |
| Comp. 2 | >100 | nd | nd |
| 3 | 50 | nd | nd |
| 4 | 51 | nd | nd |

Having described the invention in detail and by reference to the preferred embodiments thereof, it will be apparent that modifications and variations are possible without departing from the scope of the appended claims.

What is claimed is:

1. A compound of formula II:

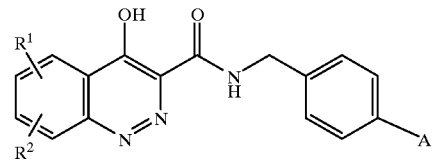

II or a pharmaceutically acceptable salt thereof wherein,
A is
 (a) Cl,
 (b) Br,
 (c) CN,
 (d) $NO_2$, or
 (e) F;
$R^1$ is
 (a) aryl,
 (b) $S(O)_m R^6$,
 (c) (C=O)$R^6$, with the proviso that if $R^6$ is $NR^7R^8$, then $R^7$ and $R^8$ do not both equal H
 (d) (C=O)$OR^9$,
 (e) cyano,
 (f) het, wherein said het is bound via a carbon atom,
 (g) Ohet,
 (h) $NR^7R^8$ with the proviso that $R^7$ and $R^8$ do not both equal H
 (i) $SR^{10}$,
 (j) Shet,
 (k) $NHCOR^{12}$,
 (l) $NHSO_2R^{12}$,
 (m) $C_{1-7}$alkyl which is partially unsaturated and optionally substituted by one or more substituents of the group $R^{11}$, $OR^{13}$, $SR^{10}$, $SR^{13}$, $NR^7R^8$, halo, (C=O)$C_{1-7}$alkyl, or $SO_m R^9$, or
 (n) $C_{1-7}$alkyl which is substituted by one or more substituents of the group $R^{11}$, $OR^{13}$, $SR^{13}$, $NR^7R^8$, halo, (C=O)$C_{1-7}$alkyl, or $SO_m R^9$;
$R^2$ is
 (a) H,
 (b) halo,
 (c) aryl,
 (d) $S(O)R_m R^6$,
 (e) (C=O)$R^6$,
 (f) (C=O)$OR^9$,
 (g) cyano,
 (h) het, wherein said het is bound via a carbon atom,
 (i) $OR^{10}$,
 (j) Ohet,
 (k) $NR^7R^8$,
 (l) $SR^{10}$, (m) Shet,
(n) NHCOR$^{12}$,
(o) NHSO$_2$R$^{12}$, or
(p) C$_{1-7}$alkyl which may be partially unsaturated and optionally substituted by one or more substituents of the group R$^{11}$, OR$^{13}$, SR$^{10}$, SR$^{13}$, NR$^7$R$^8$, halo, (C=O)C$_{1-7}$alkyl, or SO$_m$R$^9$, or
(q) R$^1$ together with R$^2$ form a carbocyclic or het which may be optionally substituted by NR$^7$R$^8$, or C$_{1-7}$alkyl which may be optionally substituted by OR$^{14}$;

R$^6$ is
(a) C$_{1-7}$alkyl,
(b) NR$^7$R$^8$
(c) aryl, or
(d) het, wherein said het is bound via a carbon atom;

R$^7$ and R$^8$ are independently
(a) H,
(b) aryl,
(c) C$_{1-7}$alkyl which may be partially unsaturated and is optionally substituted by one or more substituents selected from NR$^{10}$R$^{10}$, R$^{11}$, SO$_m$R$^9$, CONR$^{10}$R$^{10}$, or halo, or,
(d) R$^7$ and R$^8$ together with the nitrogen to which they are attached form a het;

R$^9$ is
(a) aryl,
(b) het,
(c) C$_{3-8}$cycloalkyl,
(d) methyl, or
(e) C$_{2-7}$alkyl which may be partially unsaturated and is optionally substituted by one or more substituents selected from NR$^{10}$OR$^{10}$, R$^{11}$, SH, CONR$^{10}$R$^{10}$, or halo;

R$^{10}$ is
(a) H,
(b) methyl, or
(c) C$_{2-7}$alkyl optionally substituted by OH;

R$^{11}$ is
(a) OR$^{10}$,
(b) Ohet,
(c) Oaryl,
(d) CO$_2$R$^{10}$,
(e) het,
(f) aryl,
(g) CN, or
(h) C$_{3-8}$cycloalkyl which may be partially unsaturated and optionally substituted by one or more substituents seleted from a group consisting of R$^{11}$, NR$^7$R$^8$, SO$_m$R$^9$, or C$_{1-7}$alkyl optionally substituted by R$^{11}$, NR$^7$R8, or SO$_m$R$^9$;

R$^{12}$ is
(a) H,
(b) het,
(c) aryl,
(d) C$_{3-8}$cycloalkyl,
(e) methyl, or
(f) C$_{2-7}$alkyl optionally substituted by NR$^7$R$^8$ or R$^{11}$;

R$^{13}$ is
(a) (P=O)(OR$^{14}$)$_2$;
(b) CO(CH$_2$)$_n$CON(CH$_3$)—(CH$_2$)$_n$SO$_3$$^-$M$^+$,
(c) an amino acid,
(d) C(=O)aryl, or
(e) C(=O)C$_{1-7}$alkyl optionally substituted by NR$^7$R$^8$, aryl, het, CO$_2$H, or O(CH$_2$)$_n$CO$_2$R$^{14}$;

R$^{14}$ is
(a) H, or
(b) C$_{1-7}$alkyl;

each n is independently 1, 2, 3, 4 or 5;
each m is independently 0, 1, or 2;
M is sodium, potassium, or lithium;
aryl is a phenyl radical or an ortho-fused bicyclic carbocyclic radical wherein at least one ring is aromatic;
wherein any aryl is optionally substituted with one or more substituents selected from the group consisting of halo, OH, cyano, CO$_2$R$^{14}$, CF$_3$, C$_{1-6}$alkoxy, and C$_{1-6}$ alkyl which may be further substituted by one to three SR$^{14}$, NR$^{14}$R$^{14}$, OR$^{14}$, or CO$_2$R$^{14}$ groups;
het is a four- (4), five- (5), six- (6), or seven- (7) membered saturated or unsaturated heterocyclic ring having 1, 2, or 3 heteroatoms selected from the group consisting of oxygen, sulfur, and nitrogen, which is optionally fused to a benzene ring, or any bicyclic heterocycle group;
wherein any het is optionally substituted with one or more substituents selected from the group consisting of halo, OH, cyano, phenyl, CO$_2$R$^{14}$, CF$_3$, C$_{1-6}$alkoxy, oxo, oxime, and C$_{1-6}$ alkyl which may be further substituted by one to three SR$^{14}$, NR$^{14}$R$^{14}$, OR$^{14}$, or CO$_2$R$^{14}$ groups.

2. The compound of claim 1 wherein A is Cl.
3. The compound of claim 1 wherein R$^1$ is selected from the group consisting of CH$_2$-morpholine, alkynl-CH$_2$OH, CH$_2$-(tetrahydro-2H-pyran-4-yl) and (CH$_2$)$_3$OH.
4. The compound of claim 1 which is selected from the group consisting of N-(4-chlorobenzyl)-4-hydroxy-6-(tetrahydro-2H-pyran-4-ylmethyl)-3-cinnolinecarboxamide;

N-(4-chlorobenzyl)-4-hydroxy-6-(4-morpholinylmethyl)-3-cinnolinecarboxamide;

Methyl 3-{[(4-chlorobenzyl)amino]carbonyl}-4-hydroxy-6-cinnolinecarboxylate;

N-(4-chlorobenzyl)-4-hydroxy-6-(hydroxymethyl)-3-cinnolinecarboxamide

N-(4-chlorobenzyl)-8-(cyclopropylethynyl)-4-hydroxy-6-(4-morpholinylmethyl)-3-cinnolinecarboxamide N-(4-chlorobenzyl)-8-[3-(dimethylamino)-1-propynyl]-4-hydroxy-6-(4-morpholinylmethyl)-3-cinnolinecarboxamide N-(4-chlorobenzyl)-4-hydroxy-8-(4-hydroxy-1-butynyl)-6-(4-morpholinylmethyl)-3-cinnolinecarboxaamide N-(4-chlorobenzyl)-4-hydroxy-8-[(1-hydroxycyclohexyl)ethynyl]-6-(4-morpholinylmethyl)-3-cinnolinecarboxamide N-(4-chlorobenzyl)-8-(3,3-dicyclopropyl-3-hydroxy-1-propynyl)-4-hydroxy-6-(4-morpholinylmethyl)-3-cinnolinecarboxamide N-(4-chlorobenzyl)-4-hydroxy-8-[(3S)-3-hydroxy-1-butynyl]-6-(4-morpholinylmethyl)-3-cinnolinecarboxamide 8-{3-[(aminocarbonyl)amino-3-methyl-1-butynyl}-N-(4-chlorobenzyl)-4-hydroxy-6-(4-morpholinylmethyl)-3-cinnolinecarboxamide N-(4-chlorobenzyl)-4-hydroxy-8-[3-methyl-3-(4-thioxo-1,3 ,5-triazinan-1-yl)-1-butynyl]-6-(4-morpholinylmethyl)-3-cinnolinecarboxamide N-(4-chlorobenzyl)-4-hydroxy-8-[(3R)-3-hydroxy-1-butynyl]-6-(4-morpholinylmethyl)-3-cinnolinecarboxamide N-(4-chlorobenzyl)-4-hydroxy-6-(4-morpholinylmethyl)-8-(4-[(4R)-2-oxo-1,3-oxazolidin-4-yl]-1-butynyl}-3-cinnolinecarboxamide N-(4-chlorobenzyl)-8-[3-(1,1-dioxido-4-thiomorpholinyl)-1-propynyl]-4-hydroxy-6-(4-morpholinylmethyl)-3-cinnolinecarboxamide N-(4-chlorobenzyl)-4-hydroxy-8-(5-hydroxy-1-pentynyl)-6-(4-morpholinylmethyl)-3-cinnolinecarboxamide N-(4-chlorobenzyl)-4-hydroxy-8-{[(1R,2S)-2-hydroxycyclopentyl]ethynyl}-6-(4-morpholinylmethyl)-3-cinnolinecarboxamide N-(4-chlorobenzyl)-4-hydroxy-8-(3-hydroxy-3-methyl-1-butynyl)-6-(4-morpholinylmethyl)-3-cinnolinecarboxamide N-(4-chlorobenzyl)-8-[3-(4,5-dichloro-1 H-imidazol-1-yl)-1-propynyl]-4-hydroxy-6-(4-morpholinylmethyl)-3-cinnolinecarboxamide N-(4-chlorobenzyl)-4-hydroxy-8-(3-hydroxy-1-propynyl)-6-(4-morpholinylmethyl)-3-cinnolinecarboxamide N-(4-chlorobenzyl)-8-(cyclopropylethyl)-4-hydroxy-6-(4-morpholinylmethyl)-3-cinnolinecarboxamide N-(4-chlorobenzyl)-8-[3-(dimethylamino)-1-propyl]-4-hydroxy-6-(4-morpholinylmethyl)-3-cinnolinecarboxamide N-(4-chlorobenzyl)-4-hydroxy-8-(4-hydroxy-1-butyl)-6-(4-morpholinylmethyl)-3-cinnolinecarboxamide N-(4-chlorobenzyl)-4-hydroxy-8-[(1-hydroxycyclohexyl)ethyl]-6-(4-morpholinylmethyl)-3-cinnolinecarboxamide N-(4-chlorobenzyl)-8-(3,3-dicyclopropyl-3-hydroxy-1-propyl)-4-hydroxy-6-(4-morpholinylmethyl)-3-cinnolinecarboxamide N-(4-chlorobenzyl)-4-hydroxy-8-[(3S)-3-hydroxy-1-butyl]-6-(4-morpholinylmethyl)-3-cinnolinecarboxamide 8-{3-[(aminocarbonyl)amino]-3-methyl-1-butyl}-N-(4-chlorobenzyl)-4-hydroxy-6-(4-morpholinylmethyl)-3-cinnolinecarboxamide N-(4-chlorobenzyl)-4-hydroxy-8-[3-methyl-3-(4-thioxo-1,3,5-triazinan-1-yl)-1-butyl]-6-(4-morpholinylmethyl)-3-cinnolinecarboxamide N-(4-chlorobenzyl)-4-hydroxy-8-[(3R)-3-hydroxy-1-butyl]-6-(4-morpholinylmethyl)-3-cinnolinecarboxamide N-(4-chlorobenzyl)-4-hydroxy-6-(4-morpholinylmethyl)-8-{4-[(4R)-2-oxo-1,3-oxazolidin-4-yl]-1-butyl}-3-cinnolinecarboxamide N-(4-chlorobenzyl)-8-[3-(1,1-dioxido-4-thiomorpholinyl)-1-propyl]-4-hydroxy-6-(4-morpholinylmethyl)-3-cinnolinecarboxamide N-(4-chlorobenzyl)-4-hydroxy-8-(5-hydroxy-1-pentyl)-6-(4-morpholinylmethyl)-3-cinnolinecarboxamide N-(4-chlorobenzyl)-4-hydroxy-8-{[(1R,2S)-2-hydroxycyclopentyl]ethyl}-6-(4-morpholinylmethyl)-3-cinnolinecarboxamide N-(4-chlorobenzyl)-4-hydroxy-8-(3-hydroxy-3-methyl-1-butyl)-6-(4-morpholinylmethyl)-3-cinnolinecarboxamide N-(4-chlorobenzyl)-8-[3-(4,5-dichloro-1 H-imidazol-1-yl)-1-propyl]-4-hydroxy-6-(4-morpholinylmethyl)-3-cinnolinecarboxamide N-(4-chlorobenzyl)-4-hydroxy-8-(3-hydroxy-1-propyl)-6-(4-morpholinylmethyl)-3-cinnolinecarboxamide N-(4-chlorobenzyl)-4-hydroxy-8-(3-hydroxy-1-propynyl)-3-cinnolinecarboxamide N-(4-chlorobenzyl)-4-hydroxy-8-(4-hydroxy-1-butynyl)-3-cinnolinecarboxamide N-(4-chlorobenzyl)-4-hydroxy-8-(3-hydroxy-1-propynyl)-6-(tetrahydro-2H-pyran-4-ylmethyl)-3-cinnolinecarboxamide N-(4-chlorobenzyl)-4-hydroxy-8-(phenylethynyl)-6-(tetrahydro-2H-pyran-4-ylmethyl)-3-cinnolinecarboxamide N-(4-chlorobenzyl)-4-hydroxy-8-(3-hydroxy-3-phenyl-1-propynyl)-6-(tetrahydro-2H-pyran-4-ylmethyl)-3-cinnolinecarboxamide N-(4-chlorobenzyl)-4-hydroxy-8-(4-hydroxy-1-butynyl)-6-(tetrahydro-2H-pyran-4-ylmethyl)-3-cinnolinecarboxamide N-(4-chlorobenzyl)-8-[3-(dimethylamino)-1-propynyl]-4-hydroxy-6-(tetrahydro-2H-pyran-4-ylmethyl)-3-cinnolinecarboxamide N-(4-chlorobenzyl)-4-hydroxy-8-{[(1R,2R)-1-hydroxy-2-methylcyclohexyl]ethynyl}-6-(tetrahydro-2H-pyran-4-ylmethyl)-3-cinnolinecarboxamide N-(4-chlorobenzyl)-4-hydroxy-8-{4-[(4R)-2-oxo-1,3-oxazolidin-4-yl]-1-butynyl}-6-(tetrahydro-2H-pyran-4-ylmethyl)-3-cinnolinecarboxamide N-(4-chlorobenzyl)-4-hydroxy-8-(3-hydroxy-1-propyl)-6-(tetrahydro-2H-pyran-4-ylmethyl)-3-cinnolinecarboxamide N-(4-chlorobenzyl)-4-hydroxy-8-(phenylethyl)-6-(tetrahydro-2H-pyran-4-ylmethyl)-3-cinnolinecarboxamide N-(4-chlorobenzyl)-4-hydroxy-8-(3-hydroxy-3-phenyl-1-propyl)-6-(tetrahydro-2H-pyran-4-ylmethyl)-3-cinnolinecarboxaamide N-(4-chlorobenzyl)-4-hydroxy-8-(4-hydroxy-1-butyl)-6-(tetrahydro-2H-pyran-4-ylmethyl)-3-cinnolinecarboxamide N-(4-chlorobenzyl)-8-[3-(dimethylamino)-1-propyl]-4-hydroxy-6-(tetrahydro-2H-pyran-4-ylmethyl)-3-cinnolinecarboxamide N-(4-chlorobenzyl)-4-hydroxy-8-{[(1 R,2R)-1-hydroxy-2-methylcyclohexyl]ethyl}-6-(tetrahydro-2H-pyran-4-ylmethyl)-3-cinnolinecarboxamide N-(4-chlorobenzyl)-4-hydroxy-8-{4-[(4R)-2-oxo-1,3-oxazolidin-4-yl]-1-butyl}-6-(tetrahydro-2H-pyran-4-ylmethyl)-3-cinnolinecarboxamide 5. A composition of matter comprising a pharmaceutically effective amount of a compound of formula (II):

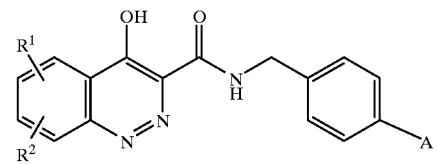

or a pharmaceutically acceptable salt thereof wherein,

A is
(a) Cl,
(b) Br, (c) CN,
(d) $NO_2$, or
(e) F;

$R^1$ is
(a) aryl,
(b) $S(O)_mR^6$,
(c) $(C=O)R^6$, with the proviso that if $R^6$ is $NR^7R^8$, then $R^7$ and $R^8$ do not both equal H
(d) $(C=O)OR^9$,
(e) cyano,
(f) het, wherein said het is bound via a carbon atom,
(g) Ohet,
(h) $NR^7R^8$ with the proviso that $R^7$ and $R^8$ do not both equal H
(i) $SR^{10}$,
(j) Shet,
(k) $NHCOR^{12}$,
(l) $NHSO_2R^{12}$,
(m) $C_{1-7}$alkyl which is partially unsaturated and optionally substituted by one or more substituents of the group $R^{11}$, $OR^{13}$, $SR^{10}$, $SR^{13}$, $NR^7R^8$, halo, (C=O)$C_{1-7}$alkyl, or $SO_mR^9$, or
(n) $C_{1-7}$alkyl which is substituted by one or more substituents of the group $R^{11}$, $OR^{13}$, $SR^{10}$, $SR^{13}$, $NR^7R^8$, halo, (C=O)$C_{1-7}$alkyl, or $SO_mR^9$;

$R^2$ is
(a) H,
(b) halo,
(c) aryl,
(d) $S(O)_mR^6$,
(e) $(C=O)R^6$,
(f) $(C=O)OR^9$,
(g) cyano,
(h) het, wherein said het is bound via a carbon atom,
(i) $OR^{10}$,
(j) Ohet,
(k) $NR^7R^8$,
(l) $SR^{10}$,
(m) Shet,
(n) $NHCOR^{12}$,
(o) $NHSO_2R^{12}$
(p) $C_{1-7}$alkyl which may be partially unsaturated and optionally substituted by one or more substituents of the group $R^{11}$, $OR^{13}$, $SR^{10}$, $SR^{13}$, $NR^7R^8$, halo, (C=O)$C_{1-7}$alkyl, or $SO_mR^9$, or
(q) $R^1$ together with $R^2$ form a carbocyclic or het which may be optionally substituted by $NR^7R^8$, or $C_{1-7}$alkyl which may be optionally substituted by $OR^{14}$;

$R^6$ is
(a) $C_{1-7}$alkyl,
(b) $NR^7R^8$
(c) aryl, or
(d) het, wherein said het is bound via a carbon atom;

$R^7$ and $R^8$ are independently
(a) H,
(b) aryl,
(c) $C_{1-7}$alkyl which may be partially unsaturated and is optionally substituted by one or more substituents selected from $NR^{10}OR^{10}$, $R^{11}$, $SO_mR^9$, $CONR^{10}R^{10}$, or halo, or,
(d) $R^7$ and $R^8$ together with the nitrogen to which they are attached form a het;

$R^9$ is
(a) aryl,
(b) het,
(c) $C_{3-8}$cycloalkyl,
(d) methyl, or
(e) $C_{2-7}$alkyl which may be partially unsaturated and is optionally substituted by one or more substituents selected from $NR^{10}R^{10}$, $R^{11}$, SH, $CONR^{10}R^{10}$, or halo;

$R^{10}$ is
(a) H,
(b) methyl, or
(c) $C_{27}$alkyl optionally substituted by OH;

$R^{11}$ is
(a) $OR^{10}$,
(b) Ohet,
(c) Oaryl,
(d) $CO_2R^{10}$,
(e) het,
(f) aryl,
(g) CN,
(h) $C_{3-8}$cycloalkyl which may be partially unsaturated and optionally substituted by one or more substituents seleted from a group consisting of $R^{11}$, $NR^7R^8$, $SO_mR^9$, or $C_{1-7}$alkyl optionally substituted by $R^{11}$, $NR^7R8$, or $SO_mR^9$;

$R^{12}$ is
(a) H,
(b) het,
(c) aryl,
(d) $C_{3-8}$cycloalkyl,
(e) methyl, or
(f) $C_{2-7}$alkyl optionally substituted by $NR^7R^8$ or $R^{11}$;

$R^{13}$ is
(a) $(P=O)(OR^{14})_2$,
(b) $CO(CH_2)_nCON(CH_3)—(CH_2)_nSO_3^-M^+$,
(c) an amino acid,
(d) C(=O)aryl, or
(e) $C(=O)C_{1-7}$alkyl optionally substituted by $NR^7R^8$, aryl, het, $CO_2H$, or $O(CH_2)_nCO_2R^{14}$;

$R^{14}$ is
(a) H, or
(b) $C_{1-7}$alkyl;

each n is independently 1, 2, 3, 4 or 5;
each m is independently 0, 1, or 2;
M is sodium, potassium, or lithium;
aryl is a phenyl radical or an ortho-fused bicyclic carbocyclic radical wherein at least one ring is aromatic;
wherein any aryl is optionally substituted with one or more substituents selected from the group consisting of halo, OH, cyano, $CO_2R^{14}$, $CF_3$, $C_{1-6}$alkoxy, and $C_{1-6}$ alkyl which may be further substituted by one to three $SR^{14}$, $NR^{14}R^{14}$, $OR^{14}$, or $CO_2R^{14}$ groups;

het is a four- (4), five- (5), six- (6), or seven- (7) membered saturated or unsaturated heterocyclic ring having 1, 2, or 3 heteroatoms selected from the group consisting of oxygen, sulfur, and nitrogen, which is optionally fused to a benzene ring, or any bicyclic heterocycle group;
wherein any het is optionally substituted with one or more substituents selected from the group consisting of halo, OH, cyano, phenyl, $CO_2R^{14}$, $CF_3$, $C_{1-6}$alkoxy, oxo, oxime, and $C_{1-6}$ alkyl which may be further substituted by one to three $SR^{14}$, $NR^{14}R^{14}$, $OR^{14}$, or $CO_2R^{14}$ groups;
and a pharmaceutically effective carrier.

6. The composition of claim 5 wherein A is Cl.
7. The composition of claim 5 wherein $R^1$ selected from the group consisting of $CH_2$-morpholine, alkynl-$CH_2OH$, $CH_2$-(tetrahydro-2H-pyran-4-yl) and $(CH_2)_3OH$.

8. The composition of claim 5 wherein said compound is selected from the group consisting of:

N-(4-chlorobenzyl)-4-hydroxy-6-(tetrahydro-2H-pyran-4-ylmethyl)-3-cinnolinecarboxamide;

N-(4-chlorobenzyl)-4-hydroxy-6-(4-morpholinylmethyl)-3-cinnolinecarboxamide;

Methyl 3-{[(4-chlorobenzyl)amino]carbonyl}-4-hydroxy-6-cinnolinecarboxylate;

N-(4-chlorobenzyl)-4-hydroxy-6-(hydroxymethyl)-3-cinnolinecarboxamide;

N-(4-chlorobenzyl)-8-(cyclopropylethynyl)-4-hydroxy-6-(4-morpholinylmethyl)-3-cinnolinecarboxamide;

N-(4-chlorobenzyl)-8-[3-(dimethylamino)-1-propynyl]-4-hydroxy-6-(4-morpholinylmethyl)-3-cinnolinecarboxamide;

N-(4-chlorobenzyl)-4-hydroxy-8-(4-hydroxy-1-butynyl)-6-(4-morpholinylmethyl)-3-cinnolinecarboxamide;

N-(4-chlorobenzyl)-4-hydroxy-8-[(1-hydroxycyclohexyl)ethynyl]-6-(4-morpholinylmethyl)-3-cinnolinecarboxainide;

N-(4-chlorobenzyl)-8-(3,3-dicyclopropyl-3-hydroxy-1-propynyl)-4-hydroxy-6-(4-morpholinylmethyl)-3-cinnolinecarboxamide;

N-(4-chlorobenzyl)-4-hydroxy-8-[(3S)-3-hydroxy-1-butynyl]-6-(4-morpholinylmethyl)-3-cinnolinecarboxamide;

8-{3-[(aminocarbonyl)amino]-3-methyl-1-butynyl}-N-(4-chlorobenzyl)-4-hydroxy-6-(4-morpholinylmethyl)-3-cinnolinecarboxamide;

N-(4-chlorobenzyl)-4-hydroxy-8-[3-methyl-3-(4-thioxo-1,3,5-triazinan-1-yl)-1-butynyl]-6-(4-morpholinylmethyl)-3-cinnolinecarboxamide;

N-(4-chlorobenzyl)-4-hydroxy-8-[(3R)-3-hydroxy-1-butynyl]-6-(4-morpholinylmethyl)-3-cinnolinecarboxamide;

N-(4-chlorobenzyl)-4-hydroxy-6-(4-morpholinylmethyl)-8-{4-[(4R)-2-oxo-1,3-oxazolidin-4-yl]-1-butynyl}-3-cinnolinecarboxamide;

N-(4-chlorobenzyl)-8-[3-(1,1-dioxido-4-thiomorpholinyl)-1-propynyl]-4-hydroxy-6-(4-morpholinylmethyl)-3-cinnolinecarboxamide;

N-(4-chlorobenzyl)-4-hydroxy-8-(5-hydroxy-1-pentynyl)-6-(4-morpholinylmethyl)-3-cinnolinecarboxamide;

N-(4-chlorobenzyl)-4-hydroxy-8-{[(1R,2S)-2-hydroxycyclopentyl]ethynyl}-6-(4-morpholinylmethyl)-3-cinnolinecarboxamide;

N-(4-chlorobenzyl)-4-hydroxy-8-(3-hydroxy-3-methyl-1-butynyl)-6-(4-morpholinylmethyl)-3-cinnolinecarboxamide;

N-(4-chlorobenzyl)-8-[3-(4,5-dichloro-1H-imidazol-1-yl)-1-propynyl]-4-hydroxy-6-(4morpholinylmethyl)3-cinnolinecarboxamide;

N-(4-chlorobenzyl)-4-hydroxy-8-(3-hydroxy-11propynyl)-6-(4-morpholinylmethyl)-3-cinnolinecarboxamide;

N-(4-chlorobenzyl)-8-[3-(dimethylamino)-1-propyl]-4-hydroxy-6-(4-morphoinylmethyl)-3-cinnolinecarboxamide;

N-(4-chlorobenzyl)-4-hydroxy-8-(4-hydroxy-1-butyl)-6-(4-morpholinylmethyl)-3-cinnolinecarboxamide;

N-(4-chlorobenzyl)-4-hydroxy-8-[(1-hydroxycyclohexyl)ethyl]-6-(4-morpholinylmethyl)-3-cinnolinecarboxamide;

N-(4-chlorobenzyl)-8-(3 ,3-dicyclopropyl-3-hydroxy-1-propyl)-4-hydroxy-6-(4-morpholinylmethyl)-3-cinnolinecarboxamide;

N-(4-chlorobenzyl)-4-hydroxy-8-[(3S)-3-hydroxy-1-butyl]-6-(4-morpholinylmethyl)-3-cinnolinecarboxamide;

8-{3-[(aminocarbonyl)amino]-3-methyl-1-butyl}-N-(4-chlorobenzyl)-4-hydroxy-6-(4-morpholinylmethyl)-3-cinnolinecarboxamide;

N-(4-chlorobenzyl)-4-hydroxy-8-[3-methyl-3-(4-thioxo-1,3,5-triazinan-1-yl)-1-butyl]-6-(4-morpholinylmethyl)-3-cinnolinecarboxamide;

N-(4-chlorobenzyl)-4-hydroxy-8-[(3R)-3-hydroxy-1-butyl]-6-(4-morpholinylmethyl)-3-cinnolinecarboxamide;

N-(4-chlorobenzyl)-4-hydroxy-6-(4-morpholinylmethyl)-8-{4-[(4R)-2-oxo-1,3-oxazolidin-4-yl]-1-butyl }-3-cinnolinecarboxamide;

N-(4-chlorobenzyl)-8-[3-(1,1-dioxido-4-thiomorpholinyl)-1-propyl]-4-hydroxy-6-(4-morpholinylmethyl)-3-cinnolinecarboxamide;

N-(4-chlorobenzyl)-4-hydroxy-8-(5-hydroxy-1-pentyl)-6-(4-morpholinylmethyl)-3-cinnolinecarboxamide;

N-(4-chlorobenzyl)-4-hydroxy-8-{[(1R,2S)-2-hydroxycyclopentyl]ethyl}-6-(4-morpholinylmethyl)-3-cinnolinecarboxamide;

N-(4-chlorobenzyl)-4-hydroxy-8-(3-hydroxy-3-methyl-1-butyl)-6-(4-morpholinylmethyl)-3-cinnolinecarboxamide;

N-(4-chlorobenzyl)-8-[3-(4,5-dichloro-1H-imidazol-1-yl)-1-propyl]-4-hydroxy-6-(4-morpholinylmethyl)-3-cinnolinecarboxamide;

N-(4-chlorobenzyl)-4-hydroxy-8-(3-hydroxy-1-propyl)-6-(4-morpholinylmethyl)-3-cinnolinecarboxamide;

N-(4-chlorobenzyl)-4-hydroxy-8-(3-hydroxy-1-propynyl)-3-cinnolinecarboxamide;

N-(4-chlorobenzyl)-4-hydroxy-8-(4-hydroxy-1-butynyl)-3-cinnolinecarboxamide;

N-(4-chlorobenzyl)-4-hydroxy-8-(3-hydroxy-1-propynyl)-6-(tetrahydro-2H-pyran-4-ylmethyl)-3-cinnolinecarboxamide;

N-(4-chlorobenzyl)-4-hydroxy-8-(phenylethynyl)-6-(tetrahydro-2H-pyran-4-ylmethyl)-3-cinnolinecarboxamide;

N-(4-chlorobenzyl)-4-hydroxy-8-(3-hydroxy-3-phenyl-1-propynyl)-6-(tetrahydro-2H-pyran-4-ylmethyl)-3-cinnolinecarboxamide;

N-(4-chlorobenzyl)-4-hydroxy-8-(4-hydroxy-1-butynyl)-6-(tetrahydro-2H-pyran-4-ylmethyl)-3-cinnolinecarboxamide;

N-(4-chlorobenzyl)-8-[3-(dimethylamino)-1-propynyl]-4-hydroxy-6-(tetrahydro-2H-pyran-4-ylmethyl)-3-cinnolinecarboxamide;

N-(4-chlorobenzyl)-4-hydroxy-8-{[(1R,2R)-1-hydroxy-2-methylcyclohexyl]ethynyl}-6-(tetrahydro-2H-pyran-4-ylmethyl)-3-cinnolinecarboxamide;

N-(4-chlorobenzyl)-4-hydroxy-8-{4-[(4R)-2-oxo-1,3-oxazolidin-4-yl]-1-butynyl}-6-(tetrahydro-2H-pyran-4-ylmethyl)-3-cinnolinecarboxamide;

N-(4-chlorobenzyl)-4-hydroxy-8-(3-hydroxy-1-propyl)-6-(tetrahydro-2H-pyran-4-ylmethyl)-3-cinnolinecarboxamide;

N-(4-chlorobenzyl)-4-hydroxy-8-(phenylethyl)-6-(tetrahydro-2H-pyran-4-ylmethyl)-3-cinnolinecarboxamide;

N-(4-chlorobenzyl)-4-hydroxy-8-(3-hydroxy-3-phenyl-1-propyl)-6-(tetrahydro-2H-pyran-4-ylmethyl)-3-cinnolinecarboxamide;

N-(4-chlorobenzyl)-4-hydroxy-8-(4-hydroxy-1-butyl)-6-(tetrahydro-2H-pyran-4-ylmethyl)-3-cinnolinecarboxamide;

N-(4-chlorobenzyl)-8-[3-(dimethylamino)-1-propyl]-4-hydroxy-6-(tetrahydro-2H-pyran-4-ylmethyl)-3-cinnolinecarboxamide;

N-(4-chlorobenzyl)-4-hydroxy-8-{[(1R,2R)-1-hydroxy-2-methylcyclohexyl]ethyl}-6-(tetrahydro-2H-pyran-4-ylmethyl)-3-cinnolinecarboxamide; and N-(4-chlorobenzyl)-4-hydroxy-8-{4-[(4R)-2-oxo-1,3-oxazolidin-4-yl]-1-butyl}-6-(tetrahydro-2H-pyran-4-ylmethyl)-3-cinnolinecarboxamide.

9. A method of treating viral infection, comprising administering to a mammal in need of such treatment, a compound of claim 1.

10. The method according to claim 9 wherein said viral infection is a herpes virus infection.

11. The method according to claim 9 wherein said mammal is a human.

12. The method according to claim 9 wherein said mammal is a livestock or companion animal.

13. The method according to claim 10 wherein the infection is herpes simplex virus type 1, 2, 6, 7, or 8, varicella zoster virus, human cytomegalovirus, or epstein-Barr virus.

14. The method according to claim 9 wherein the amount administered is from about 0.1 to about 300 mg/kg of body weight.

15. The method according to claim 14 wherein the amount administered is from about 1 to about 30 mg/kg of body weight.

16. The method according to claim 9 wherein the compound is administered parenterally, intravaginally, intranasally, topically, orally, or rectally.

17. A method for inhibiting a viral DNA polymerase, comprising contacting the polymerase with an effective inhibitory amount of a compound of claim 1.

18. The method of claim 17 wherein the polymerase and the compound are contacted in vitro.

19. The method of claim 17 wherein the polymerase and the compound are contacted in vivo.

20. The compound selected from the group consisting of:

N-(4-chlorobenzyl)-4-hydroxy-6-(4-morpholinylmethyl)-3-cinnolinecarboxamide

Methyl 3-1{[(4-chlorobenzyl)amnino]carbonyl)}-4-hydroxy-6-cinnolinecarboxylate;

N-(4-chlorobenzyl)-4-hydroxy-6-(hydroxymethyl)-3-cinnolinecarboxamide;

* * * * *